(12) United States Patent
Maeda et al.

(10) Patent No.: US 12,092,563 B2
(45) Date of Patent: Sep. 17, 2024

(54) SENSOR AND ELECTRIC DEVICE WITH THE SENSOR

(71) Applicant: Mitsubishi Electric Corporation, Tokyo (JP)

(72) Inventors: Raizo Maeda, Tokyo (JP); Tetsuo Tanaka, Tokyo (JP); Osamu Mizuno, Tokyo (JP)

(73) Assignee: MITSUBISHI ELECTRIC CORPORATION, Tokyo (JP)

( * ) Notice: Subject to any disclaimer, the term of this patent is extended or adjusted under 35 U.S.C. 154(b) by 0 days.

(21) Appl. No.: 18/566,664

(22) PCT Filed: Jun. 9, 2021

(86) PCT No.: PCT/JP2021/021924
§ 371 (c)(1),
(2) Date: Dec. 4, 2023

(87) PCT Pub. No.: WO2022/259423
PCT Pub. Date: Dec. 15, 2022

(65) Prior Publication Data
US 2024/0264070 A1    Aug. 8, 2024

(51) Int. Cl.
*G01N 17/00*  (2006.01)
*G01N 17/02*  (2006.01)
(Continued)

(52) U.S. Cl.
CPC ........... *G01N 17/04* (2013.01); *G01N 17/006* (2013.01); *G01N 17/02* (2013.01); *G01N 33/0027* (2013.01)

(58) Field of Classification Search
CPC ...... G01N 17/04; G01N 17/006; G01N 17/02; G01N 33/0027
See application file for complete search history.

(56) References Cited

U.S. PATENT DOCUMENTS 8,390,306 B2 *  3/2013  Hamann ............... G01N 17/04
324/700
9,568,455 B2 *  2/2017  Minamitani ......... G01N 17/046
(Continued)

FOREIGN PATENT DOCUMENTS

JP    2000-275201 A    10/2000
JP    2003-294606 A    10/2003
(Continued)

OTHER PUBLICATIONS

International Search Report and Written Opinion mailed on Aug. 24, 2021, received for PCT Application PCT/JP2021/021924, filed on Jun. 9, 2021, 11 pages including English Translation.
(Continued)

*Primary Examiner* — Freddie Kirkland, III
(74) *Attorney, Agent, or Firm* — XSENSUS LLP

(57) ABSTRACT

A sensor includes three structures, a measurer to measure a resistance value, an analyzer to identify the type of a corrosive gas present in an environment based on the resistance value and corrosion resistance information of the three structures, and a notification device. The three structures include a first structure, a second structure, and a third structure. The magnitude relation in corrosion resistance between the three structures differs between a first environment, a second environment, and a third environment. The corrosive gas of the first type is present and the corrosive gas of the second type is not present in the first environment. The corrosive gas of the second type is present and the corrosive gas of the first type is not present in the second environment. The corrosive gas of the first type and the corrosive gas of the second type are both present in the third environment.

20 Claims, 21 Drawing Sheets

(51) Int. Cl.
    *G01N 17/04*      (2006.01)
    *G01N 33/00*      (2006.01)

(56) References Cited

U.S. PATENT DOCUMENTS

| | | | | |
|---|---|---|---|---|
| 9,804,077 | B2 * | 10/2017 | Minamitani | G01N 27/20 |
| 10,436,701 | B2 * | 10/2019 | Minamitani | G01B 17/02 |
| 10,712,256 | B2 * | 7/2020 | Minamitani | G01N 17/002 |
| 11,460,394 | B2 * | 10/2022 | Minamitani | G01N 17/04 |
| 11,747,264 | B2 * | 9/2023 | Kawarai | G01N 17/02 |
| | | | | 324/693 |
| 2017/0350807 | A1 | 12/2017 | Minamitani | |
| 2021/0325296 | A1 | 10/2021 | Minamitani | |
| 2022/0307969 | A1 * | 9/2022 | Kawarai | G01N 27/12 |

FOREIGN PATENT DOCUMENTS

| | | |
|---|---|---|
| JP | 2006-010497 A | 1/2006 |
| JP | 2012-132718 A | 7/2012 |
| JP | 2014-153089 A | 8/2014 |
| JP | 2019-113433 A | 7/2019 |
| JP | 2019-196957 A | 11/2019 |
| JP | 2020-063988 A | 4/2020 |
| JP | 2020-125966 A | 8/2020 |
| JP | 2021-012068 A | 2/2021 |
| WO | 2016/103445 A1 | 6/2016 |
| WO | 2020/039611 A1 | 2/2020 |
| WO | 2020/255427 A1 | 12/2020 |

OTHER PUBLICATIONS

Decision to Grant mailed on Nov. 24, 2021, received for JP Application 2021-563129, 6 pages including English Translation.

Kawarai, Hisakatsu, "Development of corrosion-attack-level alert system. Estimating the corrosion speed of industrial equipment equipped with a metal corrosion sensor", Inspection Engineering, (May 1, 2020), vol. 25, No. 5, pp. 43-46 (partial English translation).

* cited by examiner

FIG.12

|  |  | FIRST STRUCTURE | SECOND STRUCTURE | THIRD STRUCTURE |
|---|---|---|---|---|
| TYPE OF METAL THIN FILM | METALLIC MATERIAL | Cu | Ag | Ag |
|  | SILICONE-BASED RESIN COATING USED | NO COATING | NO COATING | COATING USED |
| ENVIRONMENT OF EXPOSURE | FIRST ENVIRONMENT | 1 | 2 | 3 |
|  | SECOND ENVIRONMENT | 3 | 2 | 1 |
|  | THIRD ENVIRONMENT | 1 | 3 | 2 |

IN ORDER OF LOWER CORROSION RESISTANCES
(1ST-3RD POSITIONS)

FIG.16

|  |  | FIRST STRUCTURE | SECOND STRUCTURE | THIRD STRUCTURE | FOURTH STRUCTURE |
|---|---|---|---|---|---|
| TYPE OF METAL THIN FILM | METALLIC MATERIAL | Cu | Ag | Ag | Ag |
|  | SILICONE-BASED RESIN COATING USED | NO COATING | NO COATING | COATING USED | NO COATING |
|  | URETHANE-BASED RESIN COATING USED | NO COATING | NO COATING | NO COATING | COATING USED |
| ENVIRONMENT OF EXPOSURE | FIRST ENVIRONMENT | 1 | 2 | 3 | 4 |
|  | SECOND ENVIRONMENT | 4 | 2 | 1 | 3 |
|  | THIRD ENVIRONMENT | 1 | 3 | 2 | 4 |

IN ORDER OF LOWER CORROSION RESISTANCE (1ST–4TH POSITIONS)

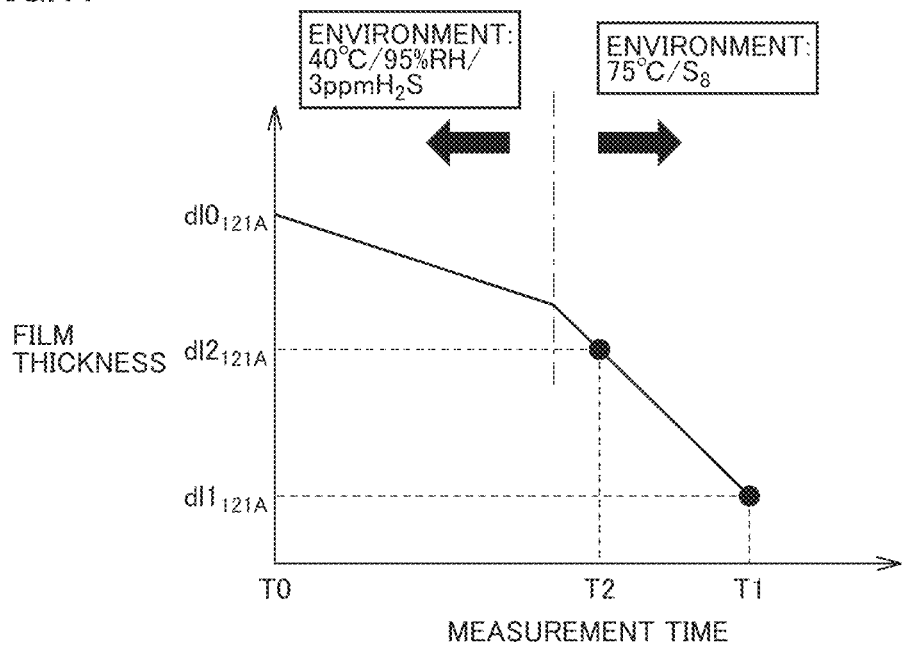

| CONDITION NO. | TEMPERATURE (°C) | HUMIDITY (%RH) | $H_2S$ CONCENTRATION (ppm) |
|---|---|---|---|
| 1 | 25 | 60 | 0.05 |
| 2 | 25 | 60 | 0.55 |
| 3 | 25 | 60 | 1.05 |
| 4 | 25 | 75 | 0.05 |
| 5 | 25 | 75 | 0.55 |
| 6 | 25 | 75 | 1.05 |
| 7 | 25 | 90 | 0.05 |
| 8 | 25 | 90 | 0.55 |
| 9 | 25 | 90 | 1.05 |
| 10 | 35 | 60 | 0.05 |
| 11 | 35 | 60 | 0.55 |
| 12 | 35 | 60 | 1.05 |
| 13 | 35 | 75 | 0.05 |
| 14 | 35 | 75 | 0.55 |
| 15 | 35 | 75 | 1.05 |
| 16 | 35 | 90 | 0.05 |
| 17 | 35 | 90 | 0.55 |
| 18 | 35 | 90 | 1.05 |
| 19 | 45 | 60 | 0.05 |
| 20 | 45 | 60 | 0.55 |
| 21 | 45 | 60 | 1.05 |
| 22 | 45 | 75 | 0.05 |
| 23 | 45 | 75 | 0.55 |
| 24 | 45 | 75 | 1.05 |
| 25 | 45 | 90 | 0.05 |
| 26 | 45 | 90 | 0.55 |
| 27 | 45 | 90 | 1.05 |

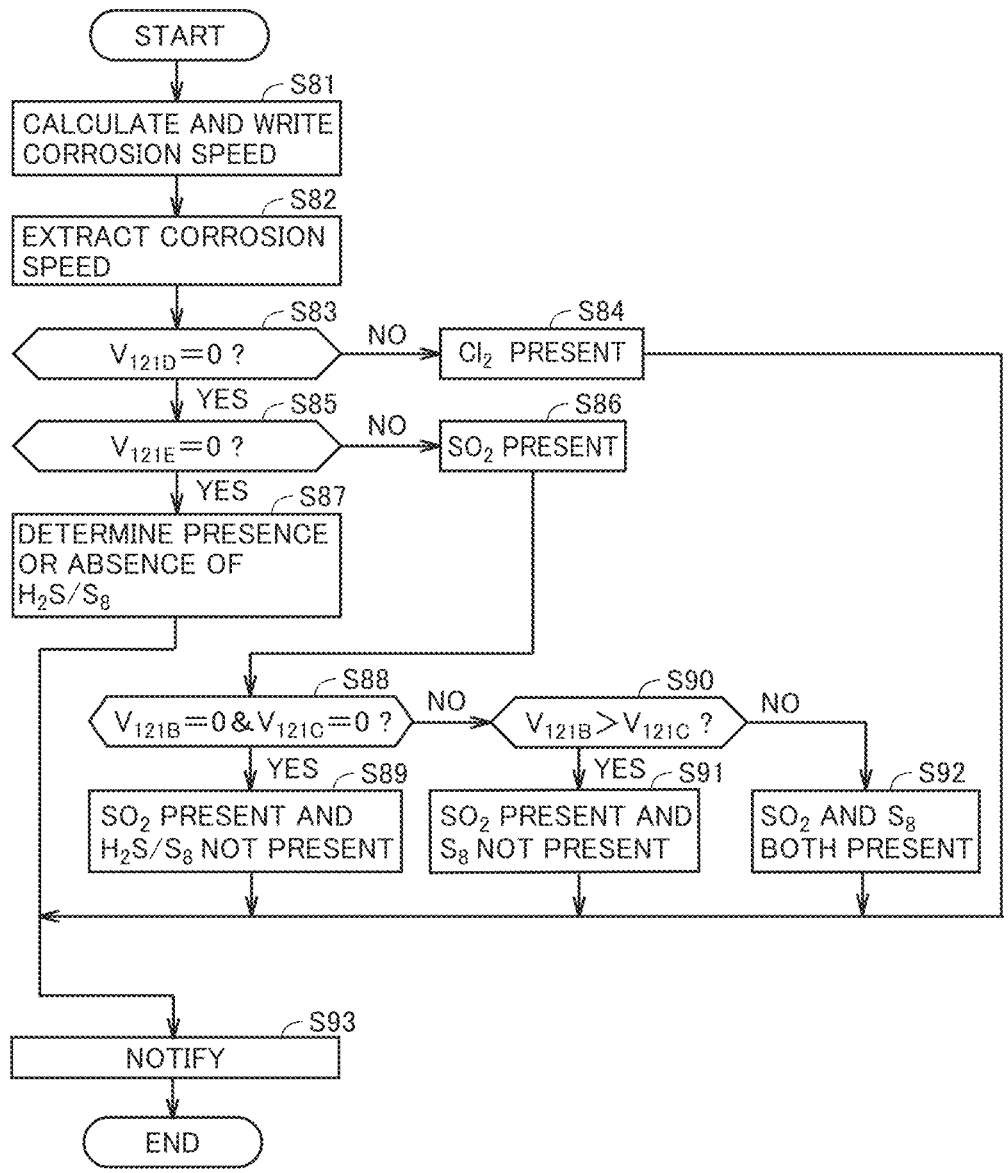

SENSOR AND ELECTRIC DEVICE WITH THE SENSOR

CROSS-REFERENCE TO RELATED APPLICATION

This application is based on PCT filing PCT/JP2021/021924, filed Jun. 9, 2021, the entire contents of which are incorporated herein by reference.

TECHNICAL FIELD

This disclosure relates to a sensor to identify the type of corrosive gas present in an environment and an electric device equipped with the sensor.

BACKGROUND ART

In case an electric device is installed in an environment where any corrosive gas is present, corrosion of the electric device may progress with time, inviting the risk of a circuit board of the device being damaged by the corrosion. An example of the risk may be breakage of metal wiring due to corrosion. To prevent such unwanted damage or breakage associated with corrosion, a technology has been proposed with an aim to grasp the degree of corrosion progressing in electric devices in environments where they are installed.

WO 2020/039611 (PTL 1) describes a corrosive environment monitoring system directed to identifying what type of corrosive gas is present in an environment. This corrosive environment monitoring system is equipped with a corrosion sensor structured with a passageway having a closed end on one side and an opening end on the other side thereof. Part of the upper and lower surfaces or the left and right surfaces of the opening is formed of a transparent substrate. A metal thin film is formed on a surface of the transparent substrate that comes into contact with the corrosive gas flowing from the opening. The corrosion sensor can observe and determine the degree of discoloration of the metal thin film through the transparent substrate and identify the type of any corrosive gas present in the environment based on correlation between the corrosive gas type and the degree of the metal thin film discoloration known from the observation.

For example, Japanese Patent Laying-Open No. 2006-10497 (PTL 2) describes an environment diagnostic tool that determines the type and concentration of any corrosive gas present in an environment where the tool is installed. The environment diagnostic tool includes a thin film. This thin film is made of at least two kinds of metal and serially changes in composition within the plane. This environment diagnostic tool determines the type and concentration of corrosive gas present in the installation environment based on the direction and speed in which the resistance neutral point between any two points with different compositions on the thin film (any three points if the thin film is made of three kinds of metals) moves due to corrosion.

CITATION LIST

Patent Literature

PTL 1: WO 2020/039611
PTL 2: Japanese Patent Laying-Open No. 2006-10497

SUMMARY OF INVENTION

Technical Problem

The technology described in PTL 1 may require a device of complexity, like camera, for image processing. The technology described in PTL 2 may need a terminal to measure the resistance neutral point. Thus, these technologies of the known art may both demand relatively large apparatuses, which may be difficult to be installed in any compact electric devices.

These technologies do not assume to determine whether any one of multiple types of corrosive gases exists alone or multiple types of corrosive gases coexist.

To address these issues of the known art, this disclosure is directed to providing a small sensor allowed to determine whether one of the first type of corrosive gas and the second type of corrosive gas is present or the first type of corrosive gas and the second type of corrosive gas are coexistent, and an electric device equipped with the sensor.

Solution to Problem

A sensor according to an aspect of this disclosure identifies the type of a corrosive gas present in an environment. The type of the corrosive gas at least includes a first type and a second type. The sensor comprises: a sensor body including at least three structures; a measurer to measure a resistance value of each of the at least three structures or a resistance value of the sensor body; an analyzer to identify the type of the corrosive gas present in the environment based on the resistance value measured by the measurer and corrosion resistance information that represents a magnitude relation in corrosion resistance between the at least three structures for each environment; and a notification device to notify a content identified by the analyzer. The at least three structures include: a first structure comprising a thin film including a first metallic material, the thin film being exposed in the environment; a second structure comprising a thin film including a second metallic material that differs from the first metallic material, the thin film being exposed in the environment; and a third structure comprising a thin film including the second metallic material, a surface of the thin film exposed in the environment being covered with a coating material. The corrosive gas of the first type and the corrosive gas of the second type each cause corrosion of the first metallic material and the second metallic material. The magnitude relation in corrosion resistance between the at least three structures differs between a first environment, a second environment, and a third environment. The corrosive gas of the first type is present and the corrosive gas of the second type is not present in the first environment. The corrosive gas of the second type is present and the corrosive gas of the first type is not present in the second environment. The corrosive gas of the first type and the corrosive gas of the second type are both present in the third environment.

An electric device according to another aspect of this disclosure is equipped with the sensor described above.

Advantageous Effects of Invention

The technology disclosed herein may successfully provide a small sensor allowed to determine whether one of the first type of corrosive gas and the second type of corrosive gas is present or the first type of corrosive gas and the second type of corrosive gas are coexistent, and an electric device equipped with the sensor.

BRIEF DESCRIPTION OF DRAWINGS

FIG. 12 is a table that shows an example of corrosion resistance information.

FIG. 16 is a table of an example of the corrosion resistance information according to a modified example of the first embodiment.

FIG. 17 is a graph drawn to describe a corrosion speed calculation method according to a second embodiment of this disclosure.

FIG. 18 is a table of exemplified test conditions applied to a test performed to formulate an estimating formula.

FIG. 29 is a flow chart of an exemplified analyzing process according to the sixth embodiment.

DESCRIPTION OF EMBODIMENTS

Embodiments of the technology disclosed herein are hereinafter described referring to the accompanying drawings. In the description below, like components and technical or structural features are illustrated with the same reference signs. Also, they are referred to likewise and have similar functional features. Such components and technical or structural features, therefore, will not be repeatedly described in detail. The embodiments and modified examples hereinafter described may be suitably selected and combined.

The corrosive gas described herein is a collective term used for sulfur-based gases, chlorine-based gases and nitrogen oxides. The sulfur-based gases are classified into sublimed sulfur ($S_8$) and other sulfur-based gases. The other sulfur-based gases may include, for example, hydrogen sulfide ($H_2S$) and sulfur dioxide ($SO_2$). The other sulfur-based gases are examples of the corrosive gas of the "first type", while sublimed sulfur is an example of the corrosive gas of the "second type". The chlorine-based gases include chlorine gas ($Cl_2$). The chlorine gas is an example of the corrosive gas of a "third type". The nitrogen oxides (NOx) may include nitrogen dioxide ($NO_2$). Silver (Ag) reacts sensitively with sublimed sulfur and chlorine gas. Copper (Cu) reacts sensitively with hydrogen sulfide, sulfur dioxide and nitrogen dioxide. Nickel (Ni) reacts sensitively with sulfur dioxide and chlorine gas. Aluminum (Al) reacts sensitively with sulfur dioxide and chlorine gas. Tin (Sn) reacts sensitively with chlorine gas.

In the description given below, a "first environment" refers to an environment where a gas included in the other sulfur-based gases is present and sublimed sulfur is not present, a "second environment" refers to an environment where sublimed sulfur is present and the other sulfur-based gases are not present, and a "third environment" refers to an environment where a gas included in the other sulfur-based gases and sublimed sulfur are coexistent and the gas included in the other sulfur-based gases has a higher concentration than the sublimed sulfur.

In first to fifth embodiments of this disclosure, the type of the corrosive gas present in a target environment is limited to a sulfur-based gas, and it is determined whether one of sublimed sulfur and any other sulfur-based gas is present or sublimed sulfur and any other sulfur-based gas are coexistent. In a sixth embodiment of this disclosure, the types of corrosive gases that can be present in a target environment are limited to a sulfur-based gas and chlorine gas, and the type of any corrosive gas present in the environment is identified.

First Embodiment

Figure 1:
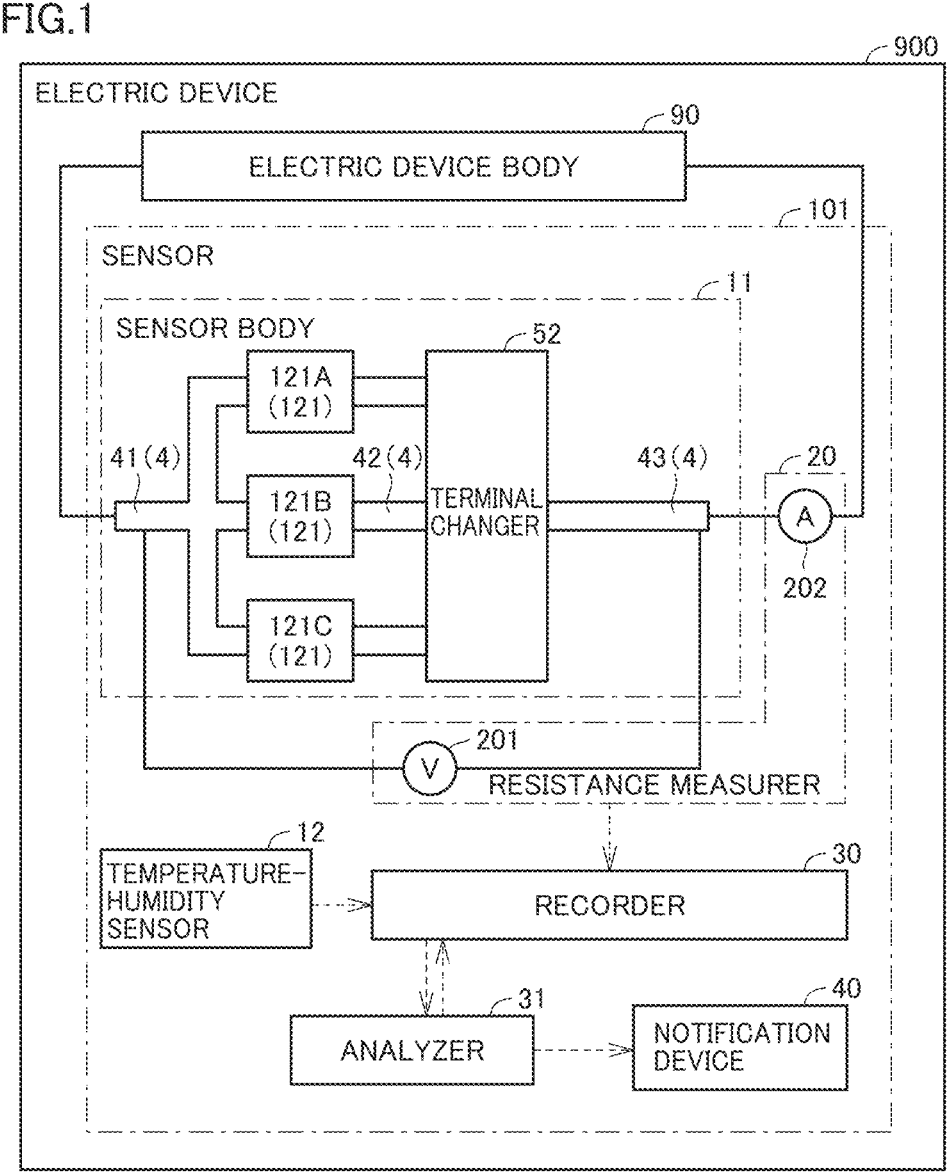
FIG. 1 is a block diagram that illustrates an electric device equipped with a sensor according to a first embodiment of this disclosure.

FIG. 1 is a block diagram that illustrates an electric device equipped with a sensor according to a first embodiment of this disclosure. With reference to FIG. 1, an electric device 900 may be a power conversion device, for example, an inverter or converter. This electric device, however, may be selected from other types of electric devices. Electric device 900 may be installed in, for example, a programmable logic controller (PLC), elevator, power generator, automobile or railway facility. In an environment where electric device 900 is thus installed and used, corrosion-induced damage may occur in electric device 900 (more specifically, electric device body 90) under the impact of corrosive gas.

Electric device 900 includes a sensor 101 and electric device body 90. Sensor 101 identifies the type of any corrosive gas present in the environment where electric device 900 (i.e., sensor 101) is installed. Sensor 101 includes a sensor body 11, a temperature-humidity sensor 12, a resistance measurer 20, a recorder 30 ("storage" as described herein), an analyzer 31, and a notification device 40.

Figure 2:
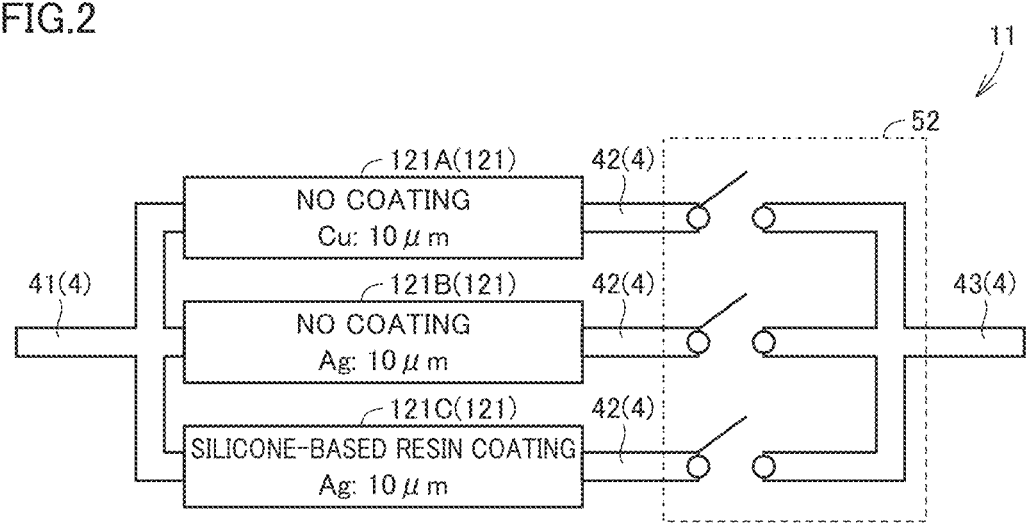
FIG. 2 is a drawing that illustrates an exemplified sensor body according to the first embodiment.
Figure 3:
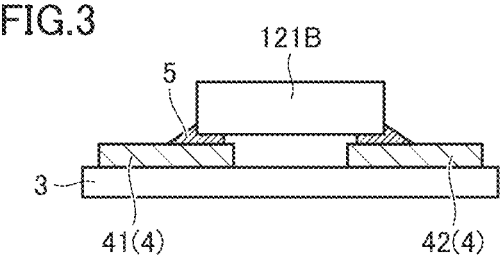
FIG. 3 is a cross-sectional view of FIG. 2 from a wiring 41, through a second structure 121B, to a wiring 42.

Structural features of sensor body 11 are described below with reference to FIGS. 2 and 3. FIG. 2 is a drawing that illustrates an exemplified sensor body according to the first embodiment. FIG. 3 is a cross-sectional view of FIG. 2 from a wiring 41, through a second structure 121B, to a wiring 42. FIG. 3 shows a structural cross section from wiring 41 to wiring 42 through second structure 121B, which is similar to a structural cross section from wiring 41, through a first structure 121A, to wiring 42, and a structural cross section from wiring 41, through a third structure 121C, to wiring 42.

With reference to FIGS. 2 and 3, sensor body 11 includes three structures (first structure 121A, second structure 121B, third structure 121C), a circuit board 3, wirings 4, a solder 5, and a terminal changer 52. In the description given below, first structure 121A, second structure 121B and third structure 121C may be collectively referred to as three structures 121.

First structure 121A includes a metal thin film, specifically, a thin film made of copper. This thin film is exposed in the environment. Copper is an example of the "first metallic material" as described herein. Copper is corrodible by sublimed sulfur and also by the other sulfur-based gases. As described above, copper sensitively reacts with the other sulfur-based gases.

Second structure 121B includes a metal thin film, specifically, a thin film made of silver. This thin film is exposed in the environment. Silver is an example of the "second metallic material" as described herein. Silver is corrodible by sublimed sulfur and also by the other sulfur-based gases. As described above, silver sensitively reacts with sublimed sulfur.

Third structure 121C includes a metal thin film, specifically, a thin film made of silver. A surface of this thin film exposed in the environment is covered with a coating material including a silicone-based resin.

The metal thin films of these three structures 121 are all 10 μm in thickness. The coating material is also 10 μm in thickness. The metal thin films of these three structures 121, however, may have different thicknesses. The metal thin films and the coating material may have different thicknesses.

Circuit board 3 may be, for example, a printed board mountable with various wirings and electronic components.

Wirings 4 include a wiring 41, three wirings 42, and a wiring 43. Wiring 41, three wirings 42, and wiring 43 are conductor wires routed on circuit board 3. Three wirings 42 are routed correspondingly to three structures 121. Wiring 41, wirings 42 and wiring 43 are spaced apart from one another. The material of wirings 4 may be selected from copper, tin, and chrome (Cr). The surfaces of wirings 4 may be coated with a resin having a very low gas permeability, for example, a resist.

The structures are each disposed so that wiring 41 is connectable to a corresponding one of wirings 42 and are mounted onto wirings 41 and 42 with solder 5. Terminal changer 52 is disposed so that one or more of three wirings 42 is connectable to wiring 43. Wirings 41 and 43 are connected to resistance measurer 20 (see FIG. 1). Terminal changer 52 is configured so that the state of connection is changeable to and from electrical connection and electrical isolation between resistance measurer 20 and each of the structures (see FIG. 1). Thus, the resistance values of first structure 121A, second structure 121B and third structure 121C may be measured separately.

Referring to FIG. 1 again, resistance measurer 20 measures the resistance values of first structure 121A, second structure 121B and third structure 121C. The resistance values measured by resistance measurer 20 are stored in recorder 30. In the example illustrated in FIG. 1, a predefined voltage is applied from electric device body 90 to between both ends of sensor body 11 (i.e., between wirings 41 and 43). Resistance measurer 20 may include a voltmeter 201 and an ammeter 202. Voltmeter 201 measures a voltage applied to between the both ends of sensor body 11. Ammeter 202 measures a current that flows through sensor body 11. Based on values presented by voltmeter 201 and ammeter 202, resistance measurer 20 calculates the resistance value of the structure currently electrically connected. Though not illustrated in the drawings, a power supply independent of electric device body 90 (for example, compact battery) may be provided to apply a voltage to between the both ends of sensor body 11.

Temperature-humidity sensor 12 measures the temperature and the humidity of a current environment in which electric device 900 exists. The temperature and the humidity measured by temperature-humidity sensor 12 are stored in recorder 30.

Analyzer 31 may include, for example, a microprocessor. Analyzer 31 identifies a type of a corrosive gas present in the environment based on the resistance values measured by resistance measurer 20 and corrosion resistance information described later. Optionally, analyzer 31 may identify a type of a corrosive gas present in the environment based on the resistance values measured by resistance measurer 20, temperature and humidity measured by temperature-humidity sensor 12, and corrosion resistance information described later. The content obtained by analyzer 31 is stored in recorder 30.

Notification device 40 includes a liquid crystal display or an LED (Light Emitting Diode) indicator. Notification device 40 notifies a user of the content obtained by analyzer 31.

Recorder 30 stores the corrosion resistance information described later. Recorder 30 associates and stores the resistance values measured by the resistance measurer 20, the temperature and humidity measured by the temperature-humidity sensor 12, and their measurement times. Recorder 30 also stores the content obtained by analyzer 31.

Electric device 900 may not be equipped with temperature-humidity sensor 12. Recorder 30 and analyzer 31 may be installed in electric device body 90 instead of sensor 101.

The three structures are hereinafter described in detail with reference to FIGS. 4 to 11.

Figure 4:
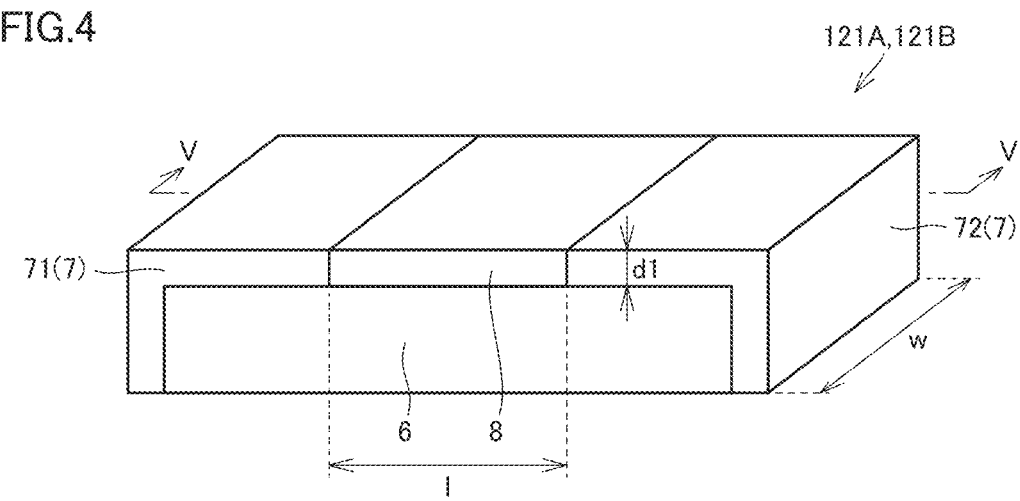
FIG. 4 is a perspective view of an exemplified first structure or second structure according to the first embodiment.
Figure 5:
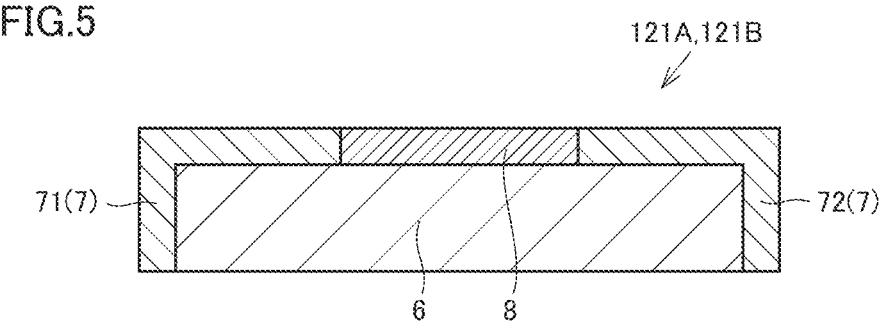
FIG. 5 is a cross-sectional view along V-V line in FIG. 4.

FIG. 4 is a perspective view of an exemplified first structure or second structure according to the first embodiment. FIG. 5 is a cross-sectional view along V-V line in FIG. 4. With reference to FIGS. 4 and 5, first structure 121A and second structure 121B each include an insulating substrate 6, an electrode pair 7, and a metal thin film 8. Insulating substrate 6 is a cuboidal substrate having insulating properties. The material of insulating substrate 6 may be selected from aluminum oxide ($Al_2O_3$), glass ($SiO_2$), and silicon wafer (Si).

Electrode pair 7 includes a pair of electrodes; first electrode 71, and second electrode 72. First electrode 71 is disposed so as to cover the upper surface in part and one lateral surface (surface on the left side in the drawing) of insulating substrate 6. Second electrode 72 is disposed so as to cover the upper surface in part and the other lateral surface (surface on the right side in the drawing) of insulating substrate 6 on the opposite side of the lateral surface provided with first electrode 71. First electrode 71 and second electrode 72 are conductor thin films, which may be formed by tin plating. First electrode 71 and second electrode 72 are electrically connected to metal thin film 8.

Metal thin film 8 has a cuboidal shape. Metal thin film 8 is disposed on the upper surface of insulating substrate 6, so that first electrode 71, metal thin film 8 and second electrode 72 are serially connected to one another in the mentioned order. The dimensions of metal thin film 8 are defined as follows; length of metal thin film 8 along a current flow direction is film length "l", length of metal thin film 8 in a direction perpendicular to the current flow direction is film width "w", and thickness of metal thin film 8 is film thickness "d1".

According to the definitions above, film width "w" and film length "l" are set to be substantially greater than film thickness d1. For instance, film thickness "d1" may be in the range of 3 to 12 μm, film width "w" may be 0.8 mm, and film length "l" may be 1.6 mm.

By thus setting the three film dimensions; film width, film length and film thickness, the film thickness may have a smallest dimension, so it is possible to narrow down the direction in which corrosion progresses to the thickness direction of the metal thin film 8. Further advantageously, such dimensions of the film width, film length and film thickness may successfully miniaturize sensor 101 (see FIG. 1).

Figure 6:
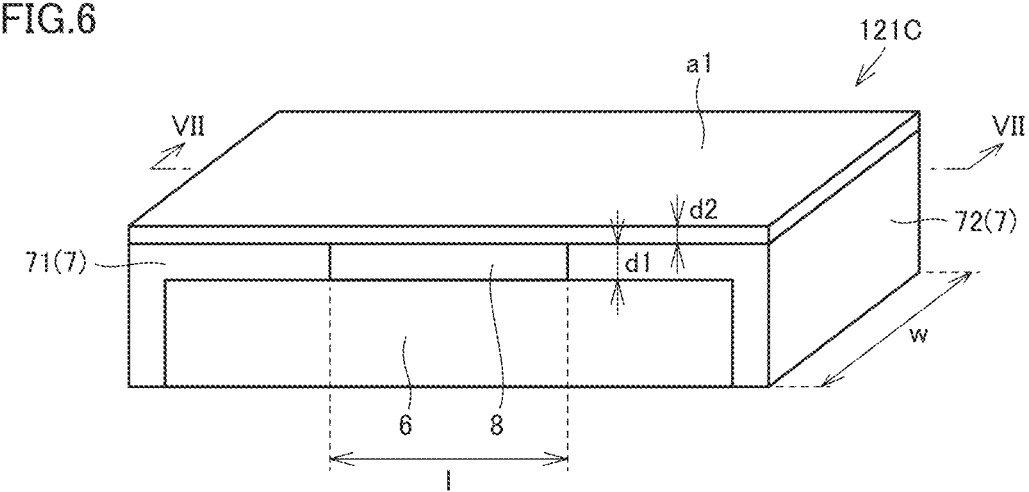
FIG. 6 is a perspective view of an exemplified third structure according to the first embodiment.
Figure 7:
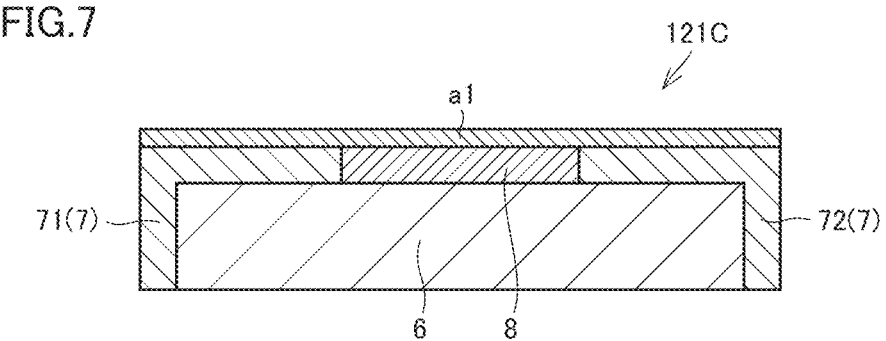
FIG. 7 is a cross-sectional view along VII-VII line in FIG. 6.

FIG. 6 is a perspective view of an exemplified third structure according to the first embodiment. FIG. 7 is a cross-sectional view along VII-VII line in FIG. 6. With reference to FIGS. 6 and 7, third structure 121C includes an insulating substrate 6, an electrode pair 7, a metal thin film 8, and a coating material a1. Third structure 121C is configured similarly to second structure 121B except inclusion of coating material a1.

Coating material a1 is used to cover a surface of metal thin film 8 exposed in the environment. Coating material a1 has a thickness d2, which may be either equal to or different from the thickness of metal thin film 8.

Coating material a1 has a gas permeability specific to sublimed sulfur. Thus, coating material a1 covering metal thin film 8 reduces the corrosion speed of this thin film (i.e., higher corrosion resistance) in the first environment where sublimed sulfur is not present. Coating material a1 covering metal thin film 8, on the other hand, increases the corrosion speed of this thin film (i.e., lower corrosion resistance) in the second environment and the third environment where sublimed sulfur is present. As a result, the magnitude relation in corrosion resistance between second structure 121B and third structure 121C differs between an environment where sublimed sulfur is not present (first environment) and an environment where sublimed sulfur is present (second or third environment).

Copper may react more sensitively than silver with the other sulfur-based gases. In other words, copper may have a lower corrosion resistance than that of silver to the other sulfur-based gases. As described above, metal thin film 8 of first structure 121A is made of copper, while metal thin film 8 of second structure 121B is made of silver. Hence, the magnitude relation in corrosion resistance between first structure 121A and second structure 121B differs between an environment where a gas included in the other sulfur-based gases is present (first or third environment) and an environment where the other sulfur-based gases are not present (second environment).

Thus, the magnitude relation in corrosion resistance between first structure 121A, second structure 121B and third structure 121C differs between the first environment, the second environment and the third environment.

The materials and thicknesses of metal thin film 8 and of the coating material a1 described so far are just a few examples. The materials and thicknesses of metal thin film 8 and of the coating material a1 may be set otherwise insofar as the magnitude relation in corrosion resistance between first structure 121A, second structure 121B and third structure 121C differs between the first environment, the second environment and the third environment.

Specifically, the material used to form metal thin film 8 may be selected from silver, copper, nickel, tin, aluminum and an alloy thereof. These metals have smaller electric resistances than most of oxides and may react with most of corrosive gases. The mentioned materials, therefore, may be suitably used to identify the type of corrosive gas present in the environment where electric device 900 is exposed.

Coating material a1 may desirably have a gas permeability or water vapor permeability specific to corrosive gas of a certain type. Examples of the coating material a1 may include coating materials including urethan-based resins, coating materials including acrylic resins, coating materials including ester-based resins, coating materials including epoxy-based resins, and agar. The gas permeability may preferably have an oxygen permeability ranging from approximately 1000 to 40000 [$cc/m^2 \cdot day$ at 20° C. (2 mm)].

FIGS. 4 to 7 shows just an exemplified shape of the metal thin film. Other possible shapes of the metal thin film are hereinafter described with reference to FIGS. 8 to 11.

Figure 8:
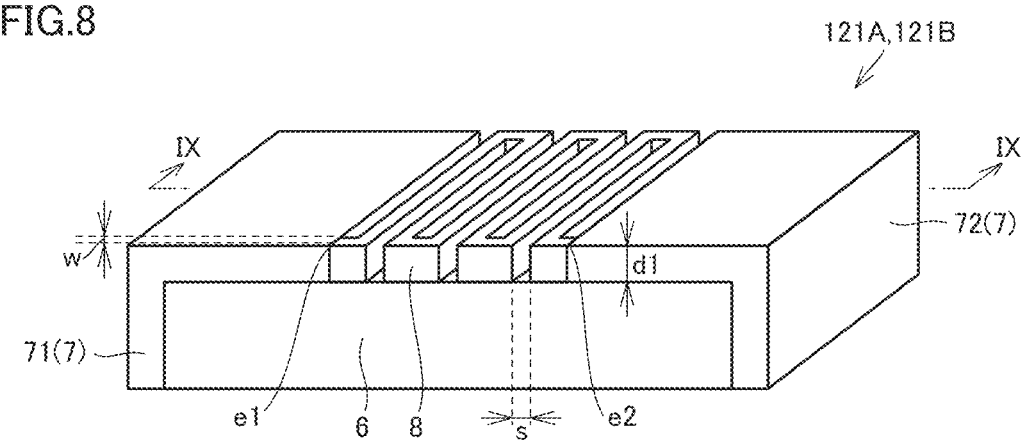
FIG. 8 is a perspective view of another exemplified first structure or second structure according to the first embodiment.
Figure 9:
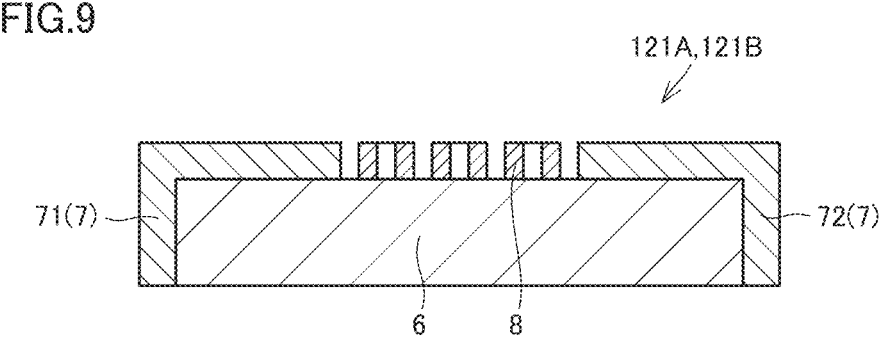
FIG. 9 is a cross-sectional view along IX-IX line in FIG. 8.
Figure 10:
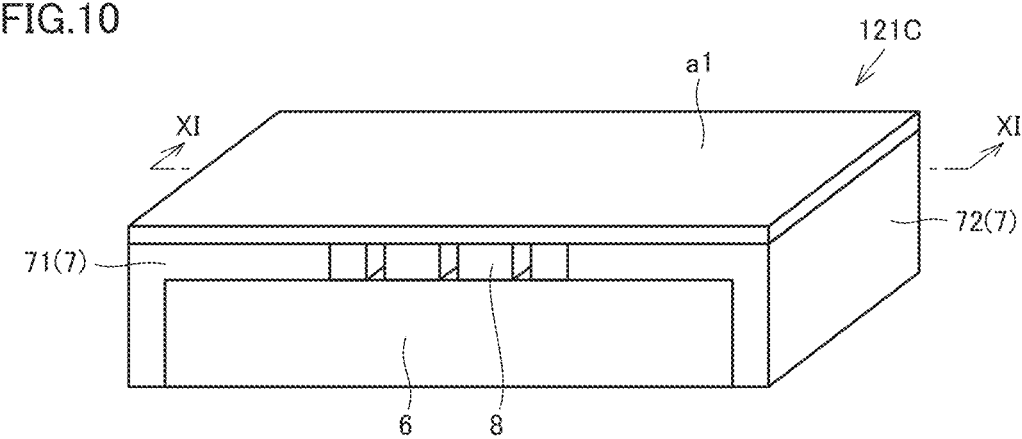
FIG. 10 is a perspective view of another exemplified third structure according to the first embodiment.
Figure 11:
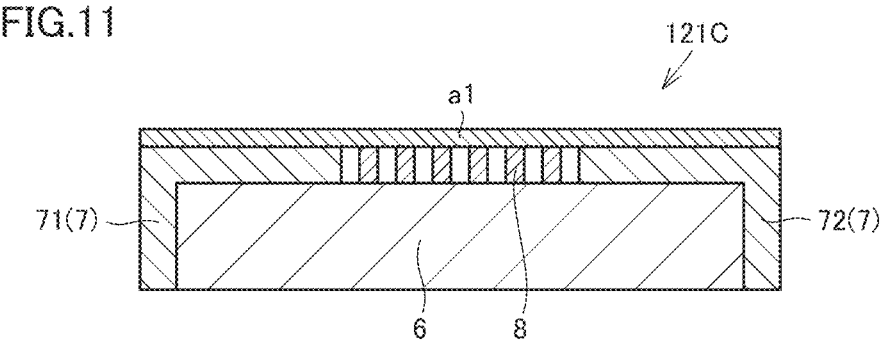
FIG. 11 is a cross-sectional view along XI-XI line in FIG. 10.

FIG. 8 is a perspective view of another exemplified first structure or second structure according to the first embodiment. FIG. 9 is a cross-sectional view along IX-IX line in FIG. 8. FIG. 10 is a perspective view of another exemplified third structure according to the first embodiment. FIG. 11 is a cross-sectional view along XI-XI line in FIG. 10.

In another example, metal thin film 8 may optionally have a tortuous shape with multiple bends at equal intervals, with reference to FIGS. 8 to 11. The structures of this example are configured similarly to the structures illustrated in FIGS. 4 to 7 except that their metal thin films 8 each have a tortuous shape with multiple bends at equal intervals.

In this example, a film length (physical length of metal thin film 8 from one end e1 to another end e2) is 1 m, film width "w" is 0.1 mm, and an interval "s" between bends of the tortuous shape is approximately 0.1 mm. By thus setting the lengths to these values, sensor 101 (see FIG. 1) may be miniaturized. These lengths and particular shape may increase an area of corrosion of metal thin film 8, allowing sensor 101 to achieve an improved precision of analysis.

While structures illustrated in FIGS. 4 and 6 are hereinafter described as typical examples of three structures, structures illustrated in FIGS. 8 and 10 may instead be used.

(Corrosion Resistance Information)

The corrosion resistance information is hereinafter described with reference mainly to FIGS. 1, 2 and 12. FIG. 12 is a table that shows an example of corrosion resistance information. The corrosion resistance information represents the magnitude relation in corrosion resistance between the structures included in sensor 101 for each environment. The structures in the table of FIG. 12 are sequentially numbered as 1, 2, 3 in the order of lower to higher per-environment corrosion resistance.

The magnitude relation in corrosion resistance between the structures included in sensor 101 for each environment may be calculated as described below. A calculation method is hereinafter described, in which the magnitude relation in corrosion resistance between three structures 121 for each environment is calculated.

First, sensor 101 including first structure 121A, second structure 121B and third structure 121C or electric device 900 mounted with this sensor 101 is exposed for a certain period of time in the first environment, the second environment and the third environment. The initial film thickness in each structure should preferably be large enough (for example, 20 μm). The certain period of time may be, for example, one month. After the certain period of time has passed, for each environment of exposure, a remaining film thickness of metal thin film 8 in each of first structure 121A, second structure 121B and third structure 121C is measured.

The remaining film thickness refers to the thickness of a portion still in metallic state of metal thin film 8 unaffected by any corrosive gas. To measure the thickness of metal thin film 8, its remaining film thickness may be actually measured through cross-sectional observation, or the thickness of a film portion in metallic state may be calculated from a volume-electric resistance correlation formula (formula 1 described later) of this metal thin film 8.

Next, an amount of reduction of metal thin film 8 in each structure is calculated based on the measured remaining film thickness.

An example is given here, in which the remaining film thickness in first structure 121A exposed in the first environment is 10 μm, the remaining film thickness in second structure 121B exposed in the first environment is 15 μm, and the remaining film thickness in third structure 121C exposed in the first environment is 18 μm. In this example, metal thin films 8 in the structures are reduced by 20 μm−10 μm=10 μm in first structure 121A, by 20 μm−15 μm=5 μm in second structure 121B, and by 20 μm−18 μm=2 μm in third structure 121C.

The corrosion resistance may be lower with a greater amount of reduction from the initial film thickness. Therefore, the magnitude relation in corrosion resistance between first, second and third structures 121A, 121B and 121C may be decided so that the structure with a greater amount of reduction from the initial film thickness has a lower corrosion resistance. In the above example, the magnitude relation in corrosion resistance between these three structures in the first environment may be decided as follows; first structure 121A<second structure 121B<third structure 121C. The magnitude relation in corrosion resistance between these three structures 121 may be decided likewise for the second environment and third environment based on the amounts of reduction from the initial film thickness.

The magnitude relation in corrosion resistance between two or more structures may be decided based on the corrosion speed or corrosion ratio. In this instance, the magnitude relation in corrosion resistance between the structures may be decided so that the structure with a higher corrosion speed or a greater corrosion ratio has a lower corrosion resistance.

The magnitude relation in corrosion resistance between two or more structures may be decided based on wire breakage situation. In this instance, the magnitude relation in corrosion resistance between the structures may be decided so that any structure undergoing wire breakage in an earlier stage than the other structures has a lower corrosion resistance.

In this embodiment, information on the magnitude relation in corrosion resistance between three structures 121 for each environment thus decided (i.e., corrosion resistance information) is stored in recorder 30. In this embodiment, analyzer 31 calculates the corrosion speed of each of three structures 121 in an environment where sensor 101 (or electric device 900) is really exposed and then determines the magnitude relation in corrosion resistance between three structures 121 based on the calculated corrosion speeds. Then, analyzer 31 identifies the type of corrosive gas based on the determined magnitude relation in corrosion resistance between three structures 121 and the magnitude relation in corrosion resistance between three structures 121 for each environment indicated by the corrosion resistance information.

FIG. 12 shows an example of the magnitude relation in corrosion resistance between three structures 121 for each environment. In case the material and thickness of metal thin film 8 and the material and thickness of coating material a1 have values that differ from those illustrated in FIG. 2, the magnitude relation in corrosion resistance between three structures 121 for each environment may naturally differ from what is illustrated in FIG. 12. Under such circumstances, the magnitude relation in corrosion resistance between three structures 121 for each environment may be decided as described above and then stored in recorder 30 as the corrosion resistance information.

(Processing Details of Sensor 101)

Figure 13:
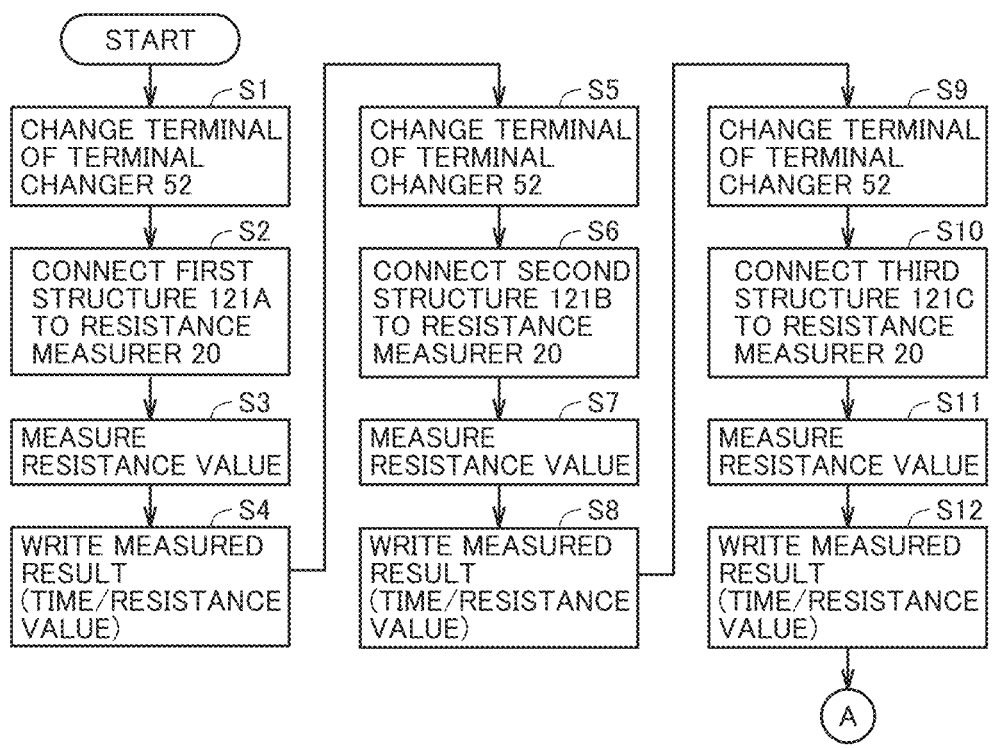
FIG. 13 is a flow chart of an exemplified analyzing process according to the first embodiment.
Figure 14:
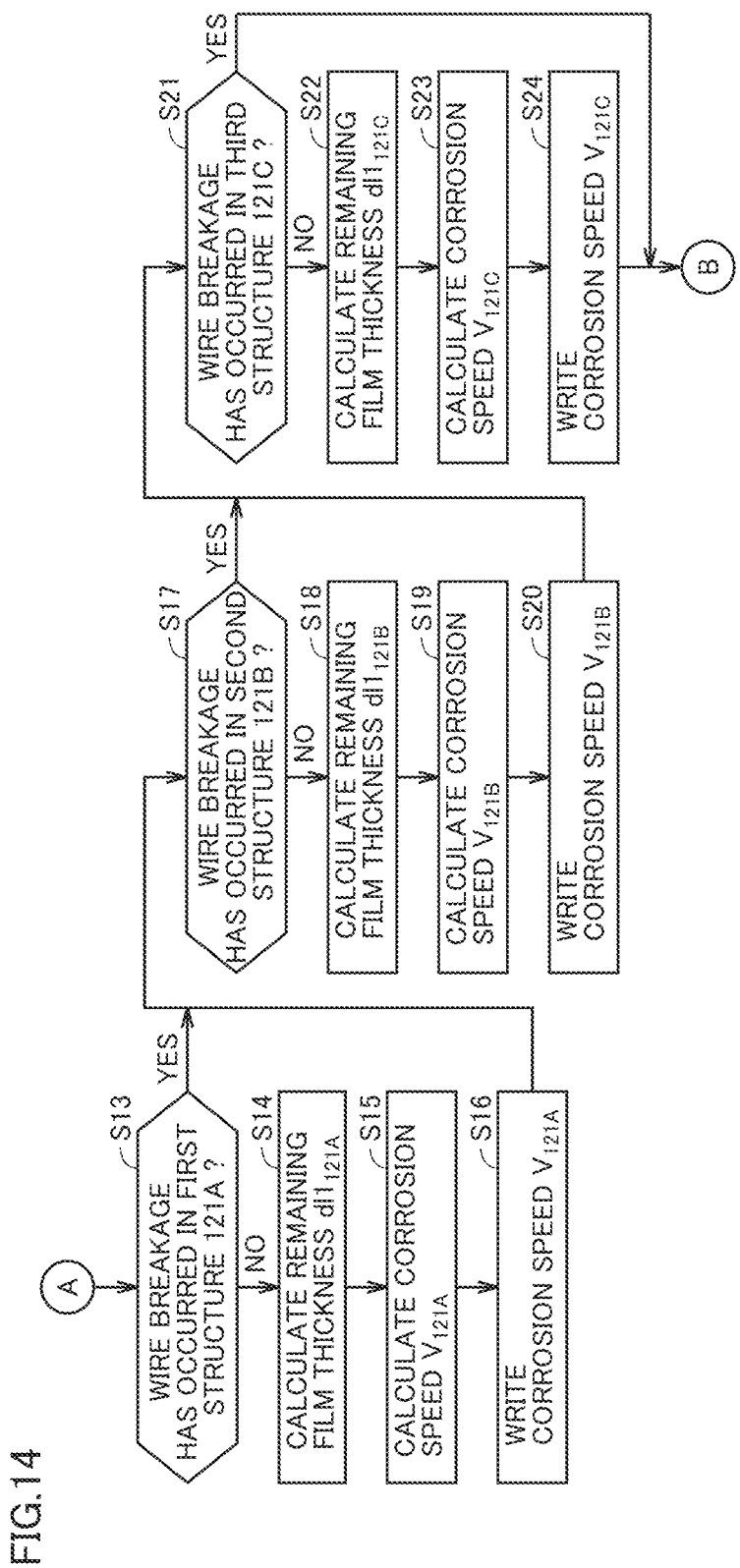
FIG. 14 is a flow chart of the exemplified analyzing process according to the first embodiment.
Figure 15:
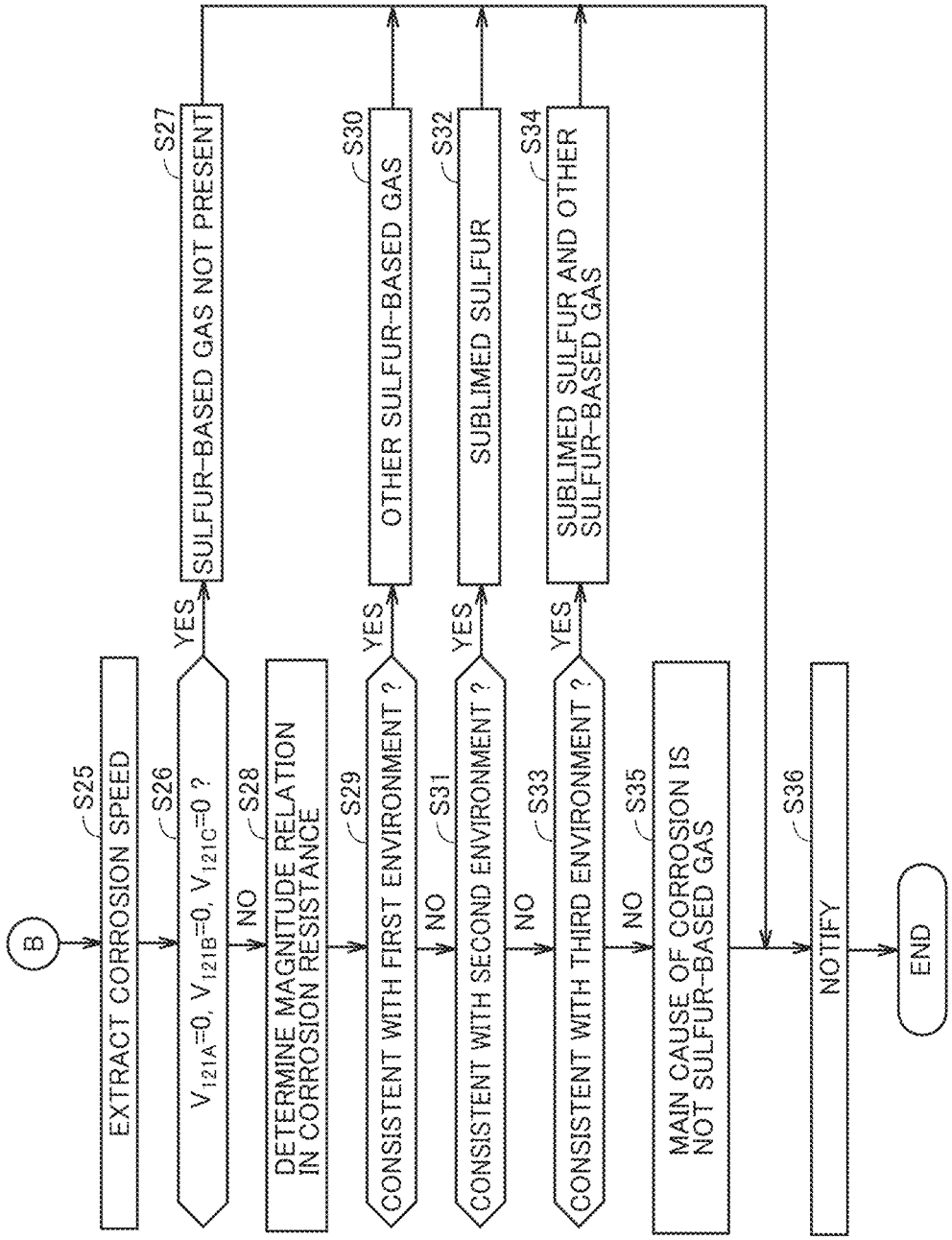
FIG. 15 is a flow chart of the exemplified analyzing process according to the first embodiment.

An analyzing process by sensor 101 is described below with reference to FIGS. 1 and 13 to 15. FIGS. 13 to 15 are flow charts of an exemplified analyzing process according to the first embodiment. The steps illustrated in FIGS. 13 to 15 are periodically invoked at predefined regular intervals from a main routine not illustrated in the drawings and then carried out by analyzer 31. The steps (hereinafter, simply "S") are basically actualized through software processing by analyzer 31, however, may be actualized through hardware processing using, for example, an electronic circuit embedded in analyzer 31.

With reference to FIGS. 13, S1 to S12 are steps of measuring a resistance value. Analyzer 31 measures resistance values at certain time intervals using a timing device, for example, a microcontroller embedded in electric device 900.

S1 to S4 are steps of measuring the resistance value of first structure 121A. In S1, analyzer 31 activates terminal changer 52 for switchover of terminals. In S2, analyzer 31 electrically connects first structure 121A and resistance measurer 20 to each other. In S3, analyzer 31 measures, using resistance measurer 20, the resistance value of first structure 121A between its both ends. In S4, analyzer 31 writes, in recorder 30, the resistance value measured by resistance measurer 20, time when the resistance value was measured (measurement time), and temperature and humidity measured by temperature-humidity sensor 12 at the time of measuring the resistance value, as the result of measurement obtained from first structure 121A. Analyzer 31 may write, in recorder 30, the resistance value measured by resistance measurer 20 and time when the resistance value was measured (measurement time) alone, as the result of measurement obtained from first structure 121A.

S5 to S8 are steps of measuring the resistance value of second structure 121B. In S5, analyzer 31 activates terminal changer 52 for switchover of terminals. In S6, analyzer 31 electrically connects second structure 121B and resistance measurer 20 to each other. In S7, analyzer 31 measures, using resistance measurer 20, the resistance value of second structure 121B between its both ends. In S8, analyzer 31 writes, in recorder 30, the resistance value measured by resistance measurer 20, time when the resistance value was measured (measurement time), and temperature and humidity measured by temperature-humidity sensor 12 at the time of measuring the resistance value, as the result of measurement obtained from second structure 121B. Analyzer 31 may write, in recorder 30, the resistance value measured by resistance measurer 20 and time when the resistance value was measured (measurement time) alone, as the result of measurement obtained from second structure 121B.

S9 to S12 are steps of measuring the resistance value of third structure 121C. In S9, analyzer 31 activates terminal changer 52 for switchover of terminals. In S10, analyzer 31 electrically connects third structure 121C and resistance measurer 20 to each other. In S11, analyzer 31 measures, using resistance measurer 20, the resistance value of third structure 121C between its both ends. In S12, analyzer 31 writes, in recorder 30, the resistance value measured by resistance measurer 20, time when the resistance value was measured (measurement time), and temperature and humidity measured by temperature-humidity sensor 12 at the time of measuring the resistance value, as the result of measurement obtained from third structure 121C. Analyzer 31 may write, in recorder 30, the resistance value measured by resistance measurer 20 and time when the resistance value was measured (measurement time) alone, as the result of measurement obtained from third structure 121C.

The results of measurement thus obtained are used to calculate the corrosion speeds of first structure 121A, second structure 121B, and third structure 121C. When S12 is over, analyzer 31 proceeds to S13 illustrated in FIG. 14.

With reference to FIGS. 14, S13 to S16 are steps of calculating the corrosion speed of first structure 121A. In S13, analyzer 31 refers to the result of measurement obtained from first structure 121A stored in recorder 30 to determine whether wire breakage has occurred or not in first structure 121A. The state in which wire breakage has occurred in one structure refers to a state in which metal thin film 8 included in the one structure has been considerably corroded and mostly replaced with a corrosion product, resulting in a soaring resistance. Then, analyzer 31 may determine that wire breakage has occurred in the one structure when its resistance value is found to be, for example, 100 times greater than an initial value.

When wire breakage has occurred in first structure 121A (YES in S13), analyzer 31 proceeds to S17. When wire breakage has not occurred in first structure 121A (NO in S13), analyzer 31 proceeds to S14.

In S14, analyzer 31 calculates a remaining film thickness $dl1_{121A}$ of metal thin film 8 in first structure 121A using the following formula 1 based on a latest resistance value $Rl1_{121A}$ of first structure 121A stored in recorder 30.

$$dl1_{121A} = \rho \times l/(w \times Rl1_{121A})[m] \qquad \text{(Formula 1)}$$

(where $dl1_{121A}$: latest film thickness (remaining film thickness) of metal thin film 8 in first structure 121A, ρ: electrical resistivity of a metallic material included in metal thin film 8, l: film length (design value) of metal thin film 8, w: film width (design value) of metal thin film 8, $Rl1_{121A}$: latest resistance value of metal thin film 8 in first structure 121A).

Analyzer 31 may use the following formula 2 to correct "ρ" with Temp11(° C.); temperature when the resistance value stored in recorder 30 was measured.

$$\rho = \rho_{20} \times (1 + k \times 10^{-3} \times (\text{Temp11} - 20))[10^{-8}\Omega \cdot m] \qquad \text{(Formula 2)}$$

(where $\rho_{20}$: electric resistivity of metal [$10^{-8}$ Ω·m] at 20° C., k: temperature coefficient of electric resistivity [$10^{-11}$ Ω·m/K]).

It should be noted that "$\rho_{20}$" and "k" have specific values for each of different types of metallic materials included in metal thin film 8, which are applied and used.

In S15, analyzer 31 calculates a corrosion speed $V_{121A}$ of first structure 121A using the following formula 3.

$$V_{121A} = (dl0_{121A} - dl1_{121A})/(T11 - T0)[m/h] \qquad \text{(Formula 3)}$$

(where $dl0_{121A}$: initial film thickness of metal thin film 8 in first structure 121A, T11: measurement time of latest resistance value $Rl1_{121A}$, T0: initial measurement time).

The initial film thickness of metal thin film 8 in each structure is prestored in recorder 30. In S16, analyzer 31 writes, in recorder 30, corrosion speed $V_{121A}$ as the latest corrosion speed of first structure 121A.

S17 to S20 are steps of calculating a corrosion speed $V_{121B}$ of second structure 121B. In S17, analyzer 31 refers to the result of measurement obtained from second structure 121B stored in recorder 30 to determine whether wire breakage has occurred or not in second structure 121B. When wire breakage has occurred in second structure 121B (YES in S17), analyzer 31 proceeds to S21. When wire breakage has not occurred in second structure 121B (NO in S17), analyzer 31 proceeds to S18.

In S18 to S20, analyzer 31 calculates corrosion speed $V_{121B}$ of second structure 121B similarly to S14 to S16 and then writes the calculated corrosion speed $V_{121B}$ in recorder 30 as the latest corrosion speed of second structure 121B.

S21 to S24 are steps of calculating a corrosion speed $V_{121C}$ of third structure 121C. In S21, analyzer 31 refers to the result of measurement obtained from third structure 121C stored in recorder 30 to determine whether wire breakage has occurred or not in third structure 121C. When wire breakage has occurred in third structure 121C (YES in S21), analyzer 31 proceeds to S25. When wire breakage has not occurred in third structure 121C (NO in S21), analyzer 31 proceeds to S22.

In S22 to S24, analyzer 31 calculates the corrosion speed $V_{121C}$ of third structure 121C similarly to S14 to S16 and then writes the calculated the corrosion speed $V_{121C}$ in recorder 30 as the latest corrosion speed of third structure 121C. When S21 or S24 is over, analyzer 31 proceeds to S25 illustrated in FIG. 15.

With reference to FIGS. 15, S25 to S36 are steps of identifying the type of corrosive gas present in the environment and notifying the identified content. In S25, analyzer 31 extracts the latest corrosion speeds $V_{121A}$, $V_{121B}$, and $V_{121C}$ from recorder 30. When it is determined that wire breakage has occurred in S13, S17 and/or S21, analyzer 31 extracts, from recorder 30, the latest one of corrosion speeds calculated before the wire breakage occurs.

In S26, analyzer 31 determines whether corrosion speeds $V_{121A}$, $V_{121B}$, and $V_{121C}$ are all zero. When corrosion speeds $V_{121A}$, $V_{121B}$, and $V_{121C}$ are all zero (YES in S26), analyzer 31 proceeds to S27. When at least one of corrosion speeds $V_{121A}$, $V_{121B}$, and $V_{121C}$ is not zero (NO in S26), analyzer 31 proceeds to S28.

In S27, analyzer 31 determines that no sulfur-based gas is present.

In S28, analyzer 31 determines the magnitude relation in corrosion resistance between three structures 121 based on the corrosion speeds $V_{121A}$, $V_{121B}$ and $V_{121C}$. Higher corrosion speed may indicate lower corrosion resistance. Analyzer 31, therefore, determines the magnitude relation in corrosion resistance between three structures 121 so that the corrosion resistance is lower with a higher corrosion speed.

In S29, analyzer 31 refers to the corrosion resistance information stored in recorder 30 to determine whether the determined magnitude relation in corrosion resistance between three structures 121 is consistent with the magnitude relation in corrosion resistance in the first environment. When the determined magnitude relation in corrosion resistance between three structures 121 is consistent with the magnitude relation in corrosion resistance in the first environment (YES in S29), analyzer 31 proceeds to S30. When the determined magnitude relation in corrosion resistance between three structures 121 is not consistent with the magnitude relation in corrosion resistance in the first environment (NO in S29), analyzer 31 proceeds to S31.

In S30, analyzer 31 identifies the type of corrosive gas present in the environment as a gas included in the other sulfur-based gases.

In S31, analyzer 31 refers to the corrosion resistance information stored in recorder 30 to determine whether the determined magnitude relation in corrosion resistance between three structures 121 is consistent with the magnitude relation in corrosion resistance in the second environment. When the determined magnitude relation in corrosion resistance between three structures 121 is consistent with the magnitude relation in corrosion resistance in the second environment (YES in S31), analyzer 31 proceeds to S32. When the determined magnitude relation in corrosion resistance between three structures 121 is not consistent with the magnitude relation in corrosion resistance in the second environment (NO in S31), analyzer 31 proceeds to S33.

In S32, analyzer 31 identifies the type of corrosive gas present in the environment as sublimed sulfur.

In S33, analyzer 31 refers to the corrosion resistance information stored in recorder 30 to determine whether the determined magnitude relation in corrosion resistance between three structures 121 is consistent with the magnitude relation in corrosion resistance in the third environment. When the determined magnitude relation in corrosion resistance between three structures 121 is consistent with the magnitude relation in corrosion resistance in the third environment (YES in S33), analyzer 31 proceeds to S34. When the determined magnitude relation in corrosion resistance between three structures 121 is not consistent with the magnitude relation in corrosion resistance in the third environment (NO in S33), analyzer 31 proceeds to S35.

In S34, analyzer 31 identifies the types of corrosive gases present in the environment as sublimed sulfur and a gas included in the other sulfur-based gases.

In S35, analyzer 31 determines that the major cause of corrosion is none of the sulfur-based gases.

In S36, analyzer 31 prompts notification device 40 to notify the obtained content. For example, analyzer 31 displays the content obtained in S27, S30, S32, S34 or S35 on a liquid crystal display.

Following on from S27, analyzer 31 may display, on the liquid crystal display, such a message as "No sulfur-based gas", "No impact from sulfur-based gas" or "Ready for continued use". Following on from S27, analyzer 31 may not display any message on the liquid crystal display.

Following on from S30, S32 or S34, analyzer 31 may display, on the liquid crystal display, such a message as "The corrosive gas is ***".

Following on from S35, analyzer 31 may display, on the liquid crystal display, such a message as "Discuss any other cause of corrosion but sulfur-based gases".

When S36 is over, analyzer 31 ends the processing steps of FIGS. 13 to 15.

When LED indicators are used as notification device 40, analyzer 31, in S36, prompts a corresponding one of the indicators to emit light to let a user know the obtained content. To be specific, analyzer 31 previously decides a portion to be illuminated or a color to be presented in each one of the indicators for different results on the environmental corrosive gas; "when sulfur-based gas is not present", "when the type of corrosive gas present in the environment is sublimed sulfur", "when the type of corrosive gas present in the environment is other sulfur-based gas", "when the types of corrosive gases present in the environment are sublimed sulfur and other sulfur-based gas", and "when corrosion factors other than sulfur-based gases can be considered". Then, analyzer 31 prompts an appropriate one of the indicators to emit light.

When a buzzer or a speaker is used as notification device 40, analyzer 31, in S36, may notify the identified content using sound.

Analyzer 31 may determine whether wire breakage has occurred or not based on the film thickness of a metallic portion of metal thin film 8 included in the structure (i.e., remaining film thickness). For example, analyzer 31 may determine that wire breakage has occurred in the structure when the remaining film thickness of metal thin film 8 is found to be less than 1% of the initial film thickness. In this instance, S13, S17 and S21 are carried out subsequent to S14, S18 and S22 respectively.

In S28, analyzer 31 may determine the magnitude relation in corrosion resistance between three structures 121 based on the corrosion ratios of three structures 121. In this instance, analyzer 31, in S15, S19 and S23, calculates the corrosion ratios instead of the corrosion speeds. In S16, S20 and S24, analyzer 31 writes, in recorder 30, the corrosion ratios instead of the corrosion speeds. In S25, analyzer 31 extracts the latest corrosion ratios from recorder 30. In S28, analyzer 31 determines the magnitude relation in corrosion resistance between three structures 121 so that the corrosion resistance is lower with a higher corrosion ratio.

Below is given the formula 4 used to calculate a corrosion ratio $P_{121A}$ of first structure 121A.

$$P_{121A}=(dl0_{121A}-dl1_{121A})/dl0_{121A} \text{[No unit]} \quad \text{(Formula 4)}$$

A corrosion ratio $P_{121B}$ of second structure 121B and a corrosion ratio $P_{121C}$ of third structure 121C may be calculated likewise.

When the corrosion ratios are calculated instead of the corrosion speeds in S15, S19 and S23, analyzer 31 determines in S26 whether corrosion ratios $P_{121A}$, $P_{121B}$, and $P_{121C}$ are all zero. When corrosion ratios $P_{121A}$, $P_{121B}$, and $P_{121C}$ are all zero (YES in S26), analyzer 31 proceeds to S27. When at least one of corrosion ratios $P_{121A}$, $P_{121B}$, and $P_{121C}$ is not zero (NO in S26), analyzer 31 proceeds to S28.

Next, verification results on usefulness of sensor 101 according to the first embodiment are hereinafter described. In working examples described below, electric device 900 equipped with sensor 101 (inverter in these examples) was exposed in a corrosive gas-present environment. Sensor 101 includes three structures 121 described above (first structure 121A, second structure 121B, and third structure 121C). The material of metal thin film 8 in first structure 121A was copper. The material of metal thin film 8 in second and third structures 121B and 121C was silver. The metal thin films 8 of these three structures 121 were all 10 μm in thickness. Coating material a1 of third structure 121C was a silicone-based resin having the oxygen permeability of 31000[cc/m$^2$·day at 20° C. (2 mm)] and having the thickness of 10 μm.

First Embodiment, First Working Example

Electric device 900 was exposed in an environment under the condition of 40° C./95% RH/3 ppm H$_2$S. On day 3 after the exposure started, the magnitude relation in corrosion speed between three structures 121 was defined as follows; first structure 121A>second structure 121B>third structure 121C. Under the condition in which H$_2$S was substituted with SO$_2$, the magnitude relation in corrosion speed in three structures 121 was defined as follows; first structure 121A>second structure 121B>third structure 121C.

This verification result demonstrates that, in an environment where H$_2$S or SO$_2$ is present and S$_8$ is not present (i.e., first environment), the magnitude relation in corrosion resistance between three structures may be defined as follows; first structure 121A<second structure 121B<third structure 121C.

First Embodiment, Second Working Example

Electric device 900 was exposed in an environment at 75° C. where S8 was present. On day 4 after the exposure started, wire breakage occurred in third structure 121C. On day 7 after the exposure started, wire breakage occurred in second structure 121B. On day 20 after the exposure started, wire breakage occurred in first structure 121A.

The corrosion resistance may be lower with an earlier occurrence of wire breakage. This verification result demonstrates that, in an environment where S8 is present and neither H$_2$S nor SO$_2$ is present (i.e., second environment), the magnitude relation in corrosion resistance between three structures may be defined as follows; first structure 121A>second structure 121B>third structure 121C.

First Embodiment, Third Working Example

Electric device 900 was exposed in an environment under the condition of 40° C./95% RH/(0.2 ppm S$_8$+3 ppm H$_2$S). On day 5 after the exposure started, wire breakage occurred in first structure 121A. On day 8 after the exposure started, wire breakage occurred in third structure 121C.

This verification result demonstrates that, in an environment where S$_8$ and H$_2$S coexist and the concentration of H$_2$S is higher than that of S$_8$ (i.e., third environment), the magnitude relation in corrosion resistance between three structures may be defined as follows; first structure 121A<third structure 121C<second structure 121B.

The verification results obtained from the first, second and third working examples of the first embodiment demonstrate that electric device 900 may be determined as being in the first environment, i.e., the type of corrosive gas present in the environment may be determined as a gas included in the other sulfur-based gases when the magnitude relation in corrosion resistance between three structures is defined as follows; first structure 121A<second structure 121B<third structure 121C.

These verification results also demonstrate that electric device 900 may be determined as being in the second environment, i.e., the type of corrosive gas present in the environment may be determined as sublimed sulfur when the magnitude relation in corrosion resistance between three structures is defined as follows; first structure 121A>second structure 121B>third structure 121C.

These verification results further demonstrate that electric device 900 may be determined as being in the third environment, i.e., in the environment may be determined as coexistence of sublimed sulfur and a gas included in the other sulfur-based gases when the magnitude relation in corrosion resistance between three structures is defined as follows; first structure 121A<third structure 121C<second structure 121B.

According to the first embodiment, sensor 101 includes three structures 121, and the magnitude relation in corrosion resistance between three structures 121 differs between first environment, second environment, and third environment. According to the first embodiment, resistance values of the structures are measured and used to specify the corrosion speeds or corrosion ratios of these structures. The magnitude relation in corrosion resistance between three structures 121 may be thus successfully determined. Further, the type of corrosive gas present in the environment may be identifiable by comparing the determined magnitude relation in corrosion resistance between three structures 121 with the corrosion resistance information stored in recorder 30. Then, it can be determined whether one of the first type of corrosive gas and the second type of corrosive gas is present or the first type of corrosive gas and the second type of corrosive gas are coexistent.

According to the first embodiment, the corrosion speed is calculated based on the latest remaining film thickness and initial film thickness of metal thin film 8. This means that the corrosion speed is calculated based on the total amount of corrosion accumulated since the manufacture of electric device 900. Thus, the type of any corrosive gas that most heavily affected electric device 900 so far after the manufacture of electric device 900 may be identified.

Sensor 101 may preferably include three or more structures. FIG. 16 presents an exemplified magnitude relation in corrosion resistance between four structures of sensor 101 for each environment.

FIG. 16 is a table of an example of corrosion resistance information according to a modified example of the first embodiment. Sensor 101 includes four structures; first structure 121A, second structure 121B, third structure 121C, and a fourth structure. The fourth structure is similar to third structure 121C except that the coating material is replaced with a urethane-based resin.

As illustrated in FIG. 16, the magnitude relation in corrosion resistance between these four structures differs between a first environment, a second environment, and a third environment. Thus, based on the magnitude relation in corrosion resistance between four structures exposed in a certain environment, the type of any corrosive gas present in this environment may be identified. Then, it can be determined whether one of the first type of corrosive gas and the second type of corrosive gas is present or the first type of corrosive gas and the second type of corrosive gas are coexistent.

Second Embodiment

An electric device according to a second embodiment of this disclosure is configured similarly to electric device 900 according to the first embodiment. An analyzing process according to the second embodiment is configured similarly to the analyzing process according to the first embodiment except that the corrosion speed is calculated differently. In the first embodiment, analyzer 31 calculates the corrosion speed based on the latest remaining film thickness and initial film thickness of metal thin film 8. In the second embodiment, analyzer 31 calculates the corrosion speed based on the latest remaining film thickness of metal thin film 8 and the remaining film thickness of metal thin film 8 at a time point that precedes the latest measurement time by an optional length of time.

A corrosion speed calculation method according to the second embodiment is hereinafter described with reference mainly to FIGS. 1, 14 and 17. FIG. 17 is a graph drawn to describe a corrosion speed calculation method according to the second embodiment.

In the second embodiment, analyzer 31 calculates, in S14, a remaining film thickness $dl1_{121A}$ of metal thin film 8 at a measurement time T1 when the latest resistance value was measured and a remaining film thickness $dl2_{121A}$ of metal thin film 8 at a measurement time T2 that precedes measurement time T1 by an optional length of time. The optional length of time may be, for example, 24 hours. The optional length of time may be set by analyzer 31 based on a user's operation. Analyzer 31 calculates remaining film thickness $dl2_{121A}$ of metal thin film 8, using the formula 1 described above, based on a resistance value $Rl2_{121A}$ at measurement time T2 stored in recorder 30. Remaining film thickness $dl1_{121A}$ may be calculated as described above.

In S15, analyzer 31 calculates, using the formula 3 described above, corrosion speed $V_{121A}$ of first structure 121A. At the time, analyzer 31 substitutes "$dl0_{121A}$" in the formula 3 with "$dl2_{121A}$", "T11" in the formula 3 with "T1", and "T0" in the formula 3 with "T2".

As with the first embodiment, analyzer 31 may calculate, using the formula 4, the corrosion ratios instead of the corrosion speeds. At the time, analyzer 31 substitutes "$dl0_{121A}$" in the formula 4 with "$dl2_{121A}$".

In S18, S19 and also in S22 and S23, analyzer 31 calculates the corrosion speed of second structure 121B and third structure 121C based on the latest remaining film thickness of metal thin film 8 and the remaining film thickness of metal thin film 8 at a point in time earlier by an optional length of time than the latest measurement time.

Thus, the magnitude relation in corrosion resistance between three structures 121 may be successfully determined based on the latest corrosion speeds. The type of any corrosive gas identifiable based on the magnitude relation, therefore, may be the type of corrosive gas present in a most recent environment. As illustrated in FIG. 17, an environment where electric device 900 is currently located may possibly be subject to change. In the example of FIG. 17, the environment where electric device 900 is installed changed from the condition of "40° C./95% RH/3 ppm H$_2$S" to the condition of "75° C./S$_8$". According to the second embodiment, however, the type of corrosive gas present in most recent environment may be identified.

Next, verification results on usefulness of sensor 101 according to the second embodiment are hereinafter described. In working examples described below, electric device 900 configured similarly to the working examples of the first embodiment was exposed in a corrosive gas-present environment.

Second Embodiment, First Working Example

Electric device 900 was exposed in an environment under the condition of 40° C./95% RH/(3 ppm H$_2$S). On day 1 after the exposure started, the magnitude relation in corrosion speed between three structures 121 was defined as follows; first structure 121A>second structure 121B>third structure 121C. Thus, the magnitude relation in corrosion resistance between three structures 121 may be defined as follows; first structure 121A<second structure 121B<third structure 121C.

Then, this electric device 900 was removed from the environment described above and exposed in an environment at 75° C. where S$_8$ was present. The magnitude relation in corrosion speed between three structures 121 after two hours passed subsequent to the environmental change until 50 hours passed subsequent to the environmental change was defined as follows; first structure 121A<second structure 121B<third structure 121C. Thus, the magnitude relation in corrosion resistance between three structures 121 may be defined as follows; first structure 121A>second structure 121B>third structure 121C.

This demonstrates that the magnitude relation in corrosion resistance between three structures 121 may change with an environmental change of electric device 900. This may also prove that the type of any corrosive gas present in a most recent environment is identifiable by grasping the magnitude relation in corrosion resistance between three structures 121 in this environment.

According to the second embodiment, the corrosion speeds within an optional range of time lengths may be successfully calculated. Thus, the magnitude relation in corrosion resistance between three structures 121 in a most recent environment may be grasped and confirmed. In a most recent environment, therefore, it can be determined whether one of the first type of corrosive gas and the second type of corrosive gas is present or the first type of corrosive gas and the second type of corrosive gas are coexistent.

Third Embodiment

An electric device according to a third embodiment of this disclosure is configured similarly to electric device 900 according to the first embodiment. In the third embodiment, analyzer 31 identifies the type of any corrosive gas present in an environment and also calculates the concentration of the identified corrosive gas.

Analyzer 31 identifies the type of any corrosive gas present in an environment in the manner described in the first or second embodiment. When the identified type of the corrosive gas is sublimed sulfur or a gas included in the other sulfur-based gases, analyzer 31 substitutes the measured value of a corrosion factor in the following estimating formula to calculate the concentration of the identified corrosive gas in the environment. The corrosion factor is a possible cause of corrosion, examples of which may include the temperature, humidity, and corrosive gas concentration.

FIG. 18 is a table of exemplified test conditions applied to a test performed to formulate an estimating formula. In this test, metal thin films similar to metal thin films 8 of sensor 101 (for example, thin films made of silver) are exposed in a plurality of model environments under different conditions. In the model environments, conditions associated with corrosion factors are differently set for the environments. In the model environments, for example, at least one of the following corrosion factors is different per environment; environmental temperature, environmental humidity, and corrosive gas concentration.

In these model environments, the following conditions, for example, may be defined and set; presence of H$_2$S, temperature range of 25 to 45° C., humidity range of 60 to 90% RH, and H$_2$S concentration range of 0.05 to 1.05 ppm. Based on the design of experiments, these defined ranges are then divided into three levels to set a plurality of test conditions. For instance, the conditions are; temperature levels of 25° C., 35° C. and 45° C., humidity levels of 60% RH, 75% RH and 90% RH, and corrosive gas concentrations of 0.05 ppm, 0.55 ppm and 1.05 ppm. Then, these conditions are variously combined to set 27 test conditions illustrated in FIG. 18.

As illustrated in FIG. 18, these test conditions include temperature-related condition, humidity-related condition, and corrosive gas concentration-related condition. An equal number of metal thin films to the number of test conditions (27 films in this example) are prepared and exposed in 27 environments specified under the different test conditions for a certain period of time. Then, corrosion speeds ($V_{c1}$-$V_{c27}$) of the metal thin films are calculated from changes over time of the amounts of corrosion of these metal thin films. Next, an estimating formula is formulated using the technique of analysis of variance based on the calculated corrosion speeds ($V_{c1}$-$V_{c27}$). The following formula 5 is an example of the estimating formula thus formulated. The formula 5 is an estimating formula used to estimate the concentration of $H_2S$.

$$V_{H2S\text{-}Ag} = 36.0 - 1.5T + 0.021T^2 - 0.12[H_2O] - 489.2[H_2S] + 396.6[H_2S]^2 + 28.2T[H_2S] - 0.39T^2[H_2S] - 25.1T[H_2S]^2 + 0.36T^2[H_2S]^2 + 0.65[H_2O][H_2S] \quad \text{(Formula 5)}$$

(where $V_{H2S\text{-}Ag} \times 10^{-4}$: corrosion speed of silver (g/($m^2 \cdot h$)), T: temperature (° C.), $[H_2O]$: humidity (% RH), and $[H_2S]$: $H_2S$ concentration (ppm)).

When the type of any corrosive gas present in the environment is identified as a gas included in the other sulfur-based gases, analyzer 31 substitutes the corrosion speed of second structure 121B, environmental temperature, and environmental humidity respectively in "$V_{H2S\text{-}Ag}$", "T", and "$H_2O$" in the formula 5 to calculate the concentration of a gas included in the other sulfur-based gases ("$H_2S$" in this example). The corrosion speed of second structure 121B substituted in the estimating formula is a value calculated by analyzer 31 to identify the type of corrosive gas present in the environment, and the environmental temperature and humidity substituted in the estimating formula are values measured by temperature-humidity sensor 12.

The estimating formula used to estimate the concentration of sublimed sulfur may be formulated by conducting a similar experiment using a model environment where sublimed sulfur is present. When the corrosive gas present in the environment is identified as sublimed sulfur, analyzer 31 calculates the concentration of sublimed sulfur by substituting the corrosion speed of second structure 121B, environmental temperature, and environmental humidity in the relevant formula.

Analyzer 31 prompts notification device 40 to notify the calculated concentration.

According to the third embodiment, the concentration of any corrosive gas present in an environment may be successfully calculated. In the test described above, the silver-made thin films are used as metal thin films similar to metal thin films 8 included in sensor 101, which may be replaced with thin films made of copper. In this instance, analyzer 31 substitutes the corrosion speed of first structure 121A in the estimating formula in place of the corrosion speed of second structure 121B.

The estimating formula described above was formulated in a model environment where only one type of corrosive gas is present. In the case of only one type of corrosive gas, the corrosive gas concentration calculated using the estimating formula may have a relatively high accuracy. However, a plurality of different corrosive gases may be likely to coexist in real environments. Thus, the corrosive gas concentration calculated using the estimating formula should be considered a reference value.

The estimating formula described above was formulated in a model environment where the temperature, humidity and corrosive gas concentration remain constant. In real environments, however, the temperature, humidity and corrosive gas concentration may often change with seasons, time slots, and/or working processes employed. When the value of a corrosion factor most recently measured is substituted in the estimating formula formulated based on the model environment, a true value of the corrosive gas concentration may be difficult to obtain. To address this issue, analyzer 31 may substitute, as the corrosion factor, an average value of the temperature degree and/or humidity in the estimating formula. This may allow analyzer 31 to calculate the corrosive gas concentration with a higher accuracy.

As in the second embodiment, analyzer 31 may substitute the corrosion speed, temperature and humidity measured in a relatively short period of time in the estimating formula. This may allow analyzer 31 to calculate the corrosive gas concentration with a higher accuracy.

Analyzer 31 may calculate the corrosive gas concentration using a well-known formula in place of the estimating formula described above.

Fourth Embodiment

In a fourth embodiment of this disclosure, analyzer 31 specifies wire breakage situation, specifically, the chronological order of wire breakage that occurred by then from changing resistance value of the sensor body and then identifies the type of corrosive gas present in the environment based on the specified chronological order.

Figure 19:
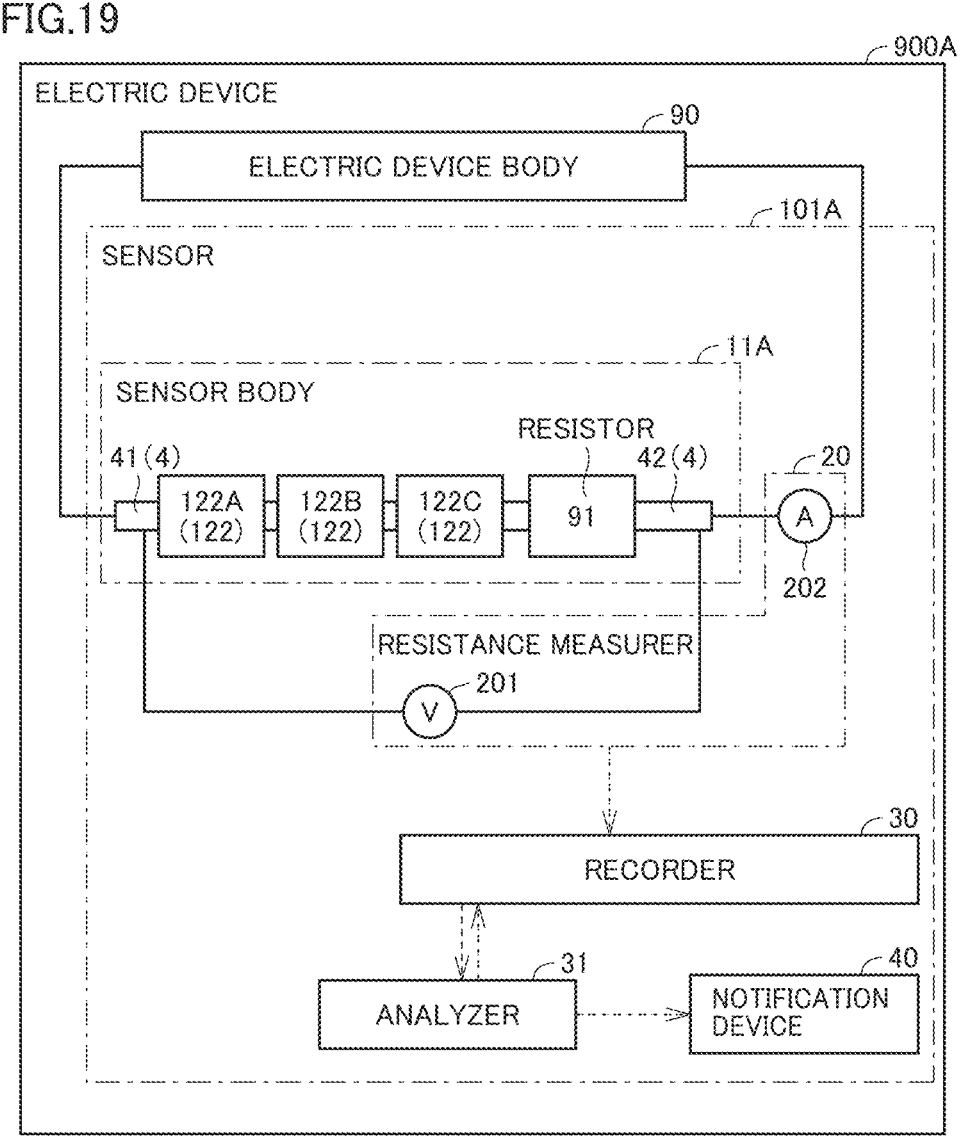
FIG. 19 is a block diagram that illustrates an electric device equipped with a sensor according to a fourth embodiment of this disclosure.

FIG. 19 is a block diagram that illustrates an electric device equipped with a sensor according to the fourth embodiment. This electric device 900A is configured similarly to electric device 900 of the first embodiment (see FIG. 1) except the following differences; its sensor body is differently configured, and temperature-humidity sensor 12 (see FIG. 1) is not installed. Electric device 900A includes a sensor 101A and electric device body 90. Sensor 101A includes a sensor body 11A, resistance measurer 20, recorder 30, analyzer 31, and notification device 40.

Sensor body 11A includes three structures (first structure 122A, second structure 122B, third structure 122C), a resistor 91, and wirings 4. In the description given below, first structure 122A, second structure 122B and third structure 122C may be collectively referred to as three structures 122. Wirings 4 include a wiring 41 and a wiring 42. Wirings 4 are routed on a circuit board. Three structures 122 and resistor 91 are mounted onto wirings 41 and 42 by soldering so that wirings 41 and 42 are connectable to each other. Three structures 122 and resistor 91 are serially connected to between wirings 41 and 42.

Figure 20:
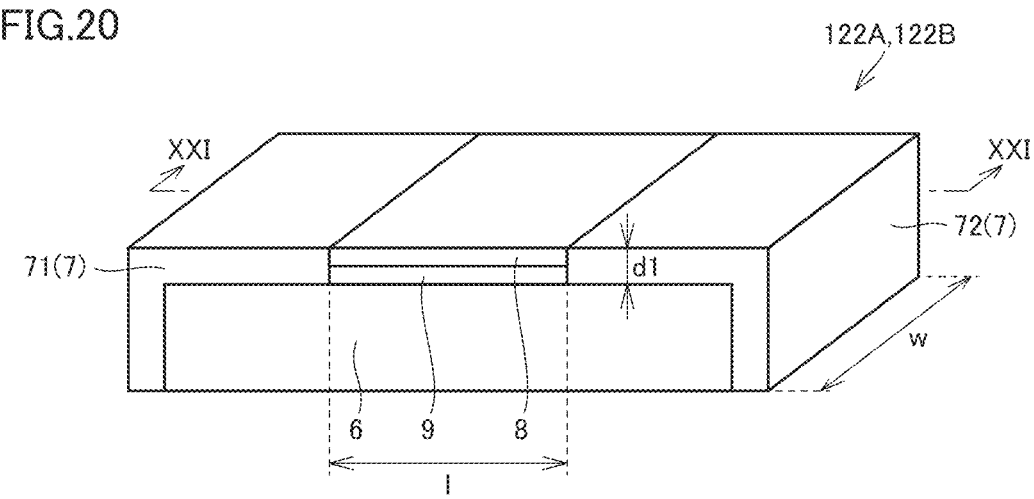
FIG. 20 is a perspective view of exemplified first and second structures according to the fourth embodiment.
Figure 21:
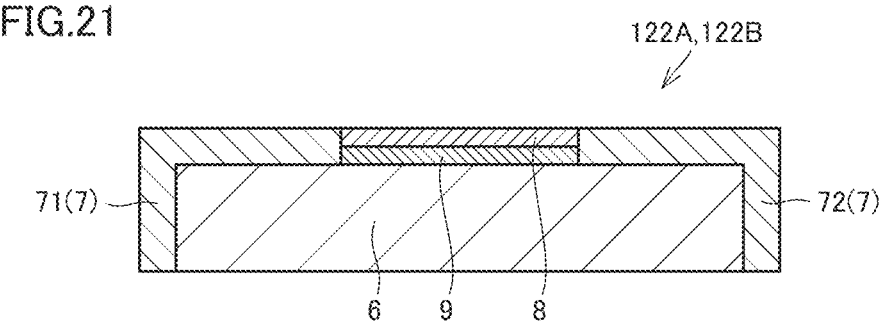
FIG. 21 is a cross-sectional view along XXI-XXI line in FIG. 20.

FIG. 20 is a perspective view of exemplified first and second structures according to the fourth embodiment. FIG. 21 is a cross-sectional view along XXI-XXI line in FIG. 20. With reference to FIGS. 20 and 21, first structure 122A and second structure 122B are configured similarly to first structure 121A and second structure 121B described above except that first structure 122A and second structure 122B each include resistor 9. First structure 122A and second structure 122B each include insulating substrate 6, electrode pair 7, metal thin film 8, and resistor 9.

Metal thin film 8 and resistor 9 are connected in parallel to between first electrode 71 and second electrode 72. Metal thin film 8 is disposed at a position on the outer side than resistor 9 and is exposed in an environment. The resistance value of metal thin film 8 is set to a significantly smaller value than that of resistor 9.

Resistor 9 is very resistant to corrosive gases and is hardly corrodible by corrosive gases. The material of resistor 9 may be selected from oxide semiconductors (for example, ruthenium oxide ($RuO_2$)). The resistance value of resistor 9 may preferably be higher than the resistance value of metal thin film 8.

Figure 22:
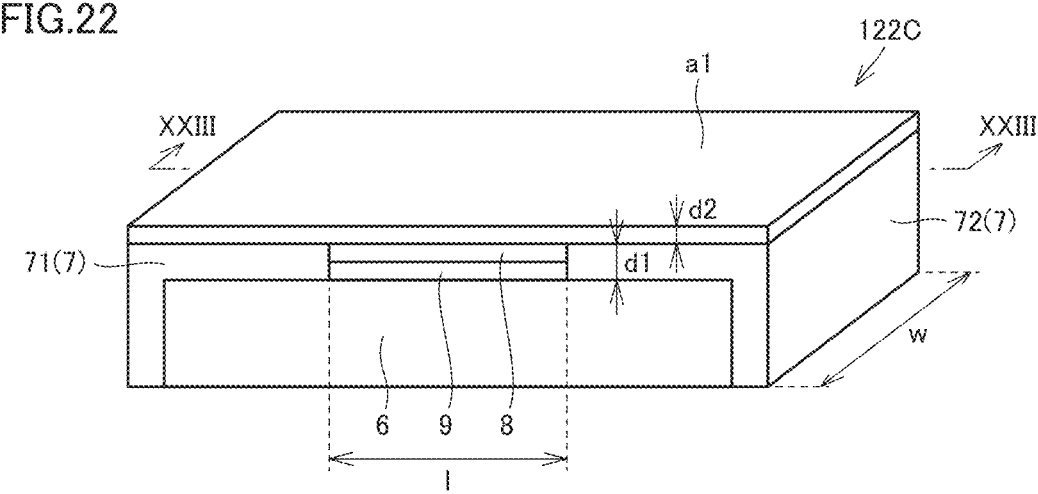
FIG. 22 is a perspective view of an exemplified third structure according to the fourth embodiment.
Figure 23:
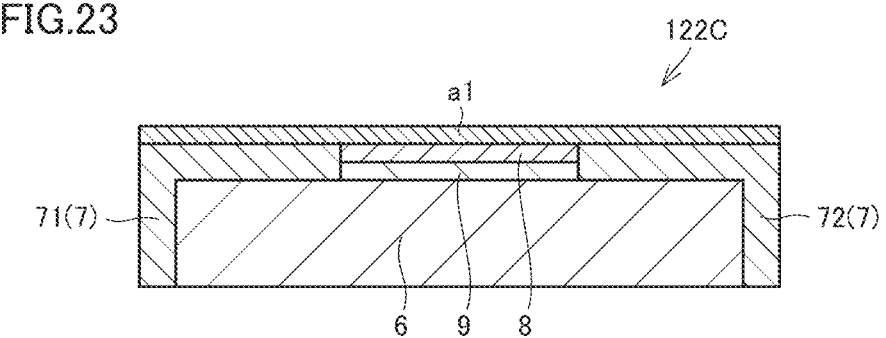
FIG. 23 is a cross-sectional view along XXIII-XXIII line in FIG. 22.

FIG. 22 is a perspective view of an exemplified third structure according to the fourth embodiment. FIG. 23 is a cross-sectional view along XXIII-XXIII line in FIG. 22. With reference to FIGS. 22 and 23, third structure 122C is configured similarly to third structure 121C except that third structure 122C includes resistor 9. Third structure 122C includes insulating substrate 6, electrode pair 7, metal thin film 8, resistor 9, and coating material a1. Coating material a1 is used to cover a surface of metal thin film 8 exposed in the environment.

With reference to FIG. 20 again, resistance value changes that occur before and after wire breakage are described using second structure 122B as a typical example. In this example, the material of metal thin film 8 in second structure 122B is silver, and this metal film has the following dimensions; film width "w" of 0.5 mm, film length "1" of 1 mm, and film thickness "d1" of 5 μm. Further, the material of resistor 9 in second structure 122B is ruthenium oxide, and its resistance value $R_R$ is 400Ω. Metal thin film 8 and resistor 9 are connected in parallel to each other. An electric resistivity "ρ" of silver included in metal thin film 8 is $1.6×10^{-8}$ at 20° C.

In second structure 122B in an environment at 20° C., its initial resistance value $R_{O2}$ may be calculated using the formula 1 and the following formula 6. Initial resistance value $R_{O2}$ of second structure 122B thus calculated is substantially equal to a resistance value $R_O$ of metal thin film 8.

$$R_{O2}=R_O×R_R/(R_O+R_R)=6.4×10^{-3} Ω \quad \text{(Formula 6)}$$

(where $R_O$: resistance value of metal thin film $8=1.6×10^{-8}×1×10^{-3}/(0.5×10^{-3}×5×10^{-6})=6.4×10^{-3} Ω$, $R_R=400Ω$).

This second structure 122B is kept exposed in the environment to calculate the resistance value at the time of breakage of metal thin film 8. Metal thin film 8, as progressively corroded, transforms from the metallic state into a corrosion product. Therefore, breakage of metal thin film 8 does not occur physically. The corrosion product generated then, however, has a resistance 100 thousand times greater than a typical metal resistance. Thus, metal thin film 8 is electrically insulated, which may be, in fact, regarded as breakage. With a resistance value $R_O'$ of metal thin film 8 being infinite, a resistance value $R_{O2}'$ of second structure 122B is calculated using the following formula 7. Resistance value $R_{O2}'$ of second structure 122B thus calculated is substantially equal to resistance value $R_R$ of resistor 9 in second structure 122B.

$$R_{O2}'=R_O'×R_R/(R_O'+R_R)=R_R/(1+R_R/R_O')≈R_R=400Ω \quad \text{(Formula 7)}$$

Thus, initial resistance value $R_{O2}$ of second structure 122B is substantially equal to resistance value $R_O$ of metal thin film 8, and resistance value $R_{O2}'$ of second structure 122B subsequent to wire breakage is substantially equal to resistance value $R_R$ of resistor 9. The same applies to first structure 122A and third structure 122C. In this embodiment, the resistance value of resistor 9 in an optional one of three structures 122 is so set that differs from a resistance value of resistor 9 in each of the other structures and that differs from a total of respective resistance values of resistors 9 in optionally selected ones of the other structures. With the resistance values being set to such values, any structure undergoing wire breakage may be identified from resistance value changes of sensor body 11A (see FIG. 19).

Figure 24:
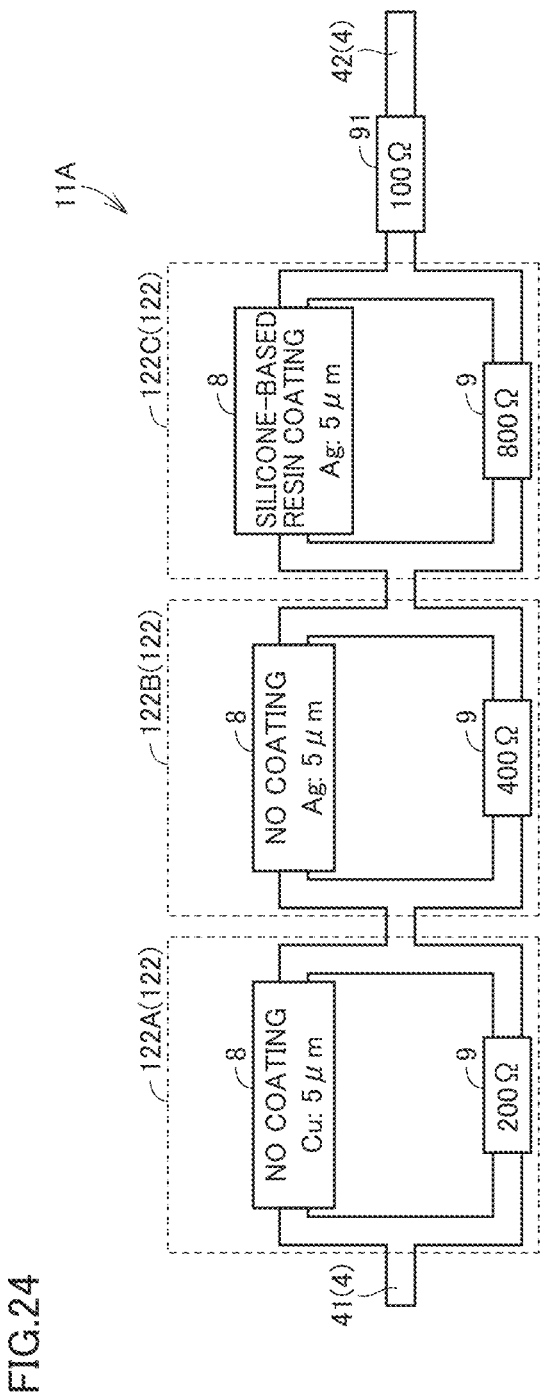
FIG. 24 is a drawing that illustrates an exemplified sensor body according to the fourth embodiment.

FIG. 24 is a drawing that illustrates an exemplified sensor body according to the fourth embodiment. Sensor body 11A includes three structures 122, resistor 91, and wirings 41 and 42.

First structure 122A includes metal thin film 8, specifically, a thin film made of copper and further incudes resistor 9. Metal thin film 8 is exposed in the environment. The resistance value of resistor 9 is set to 200Ω.

Second structure 122B includes metal thin film 8, specifically, a thin film made of silver and further incudes resistor 9. Metal thin film 8 is exposed in the environment. The resistance value of resistor 9 is set to 400Ω.

Third structure 122C includes metal thin film 8, specifically, a thin film made of silver and further incudes resistor 9. A surface of metal thin film 8 exposed in the environment is covered with a coating material including a silicone-based resin. The resistance value of resistor 9 is set to 800Ω.

The metal thin films of these three structures 122 are all 5 μm in thickness. The coating material is also 5 μm in thickness. Instead, the metal thin films of these three structures 122 may have different thicknesses. The metal thin films and the coating material may have different thicknesses.

The coating material including a silicone-based resin has a gas permeability specific to sublimed sulfur. As a result, a magnitude relation in corrosion resistance between second structure 122B and third structure 122C differs between an environment where sublimed sulfur is not present (first environment) and an environment where sublimed sulfur is present (second or third environment).

Copper may react more sensitively than silver with the other sulfur-based gases. As a result, a magnitude relation in corrosion resistance between first structure 122A and second structure 122B differs between an environment where a gas included in the other sulfur-based gases is present (first or third environment) and an environment where the other sulfur-based gases are not present (second environment).

Thus, a magnitude relation in corrosion resistance between first structure 122A, second structure 122B and third structure 122C differs between the first environment, the second environment, and the third environment.

In this embodiment, information on the magnitude relation in corrosion resistance between three structures 122 for each environment (i.e., corrosion resistance information) is stored in recorder 30. In this embodiment, analyzer 31 specifies the chronological order of wire breakage that occurred by then based on resistance value changes of sensor body 11A in an environment where sensor 101A (or electric device 900A) is really exposed. Then, analyzer 31 determines the magnitude relation in corrosion resistance between three structures 122 based on the chronological order of wire breakage that occurred by then. Then, analyzer 31 identifies the type of any corrosive gas based on the determined magnitude relation in corrosion resistance between three structures 122 and the magnitude relation in corrosion resistance between three structures 122 for each environment indicated by the corrosion resistance information.

The materials and thicknesses of metal thin film 8 and of the coating material described so far are just a few examples. The materials and thicknesses of metal thin film 8 and of the coating material may be set otherwise insofar as the magnitude relation in corrosion resistance between first structure 122A, second structure 122B and third structure 122C differs between the first environment, the second environment, and the third environment.

The resistance values of resistors 9 of FIG. 24 are illustrated as a few examples. The resistance value of resistor 9 in an optional one of three structures 122 is so set that differs from a resistance value of resistor 9 in each of the other structures and that differs from a total of respective resistance values of resistors 9 in optionally selected ones of the other structures.

The resistance value of resistor 91 illustrated in FIG. 24 is just an example.

Figure 25:
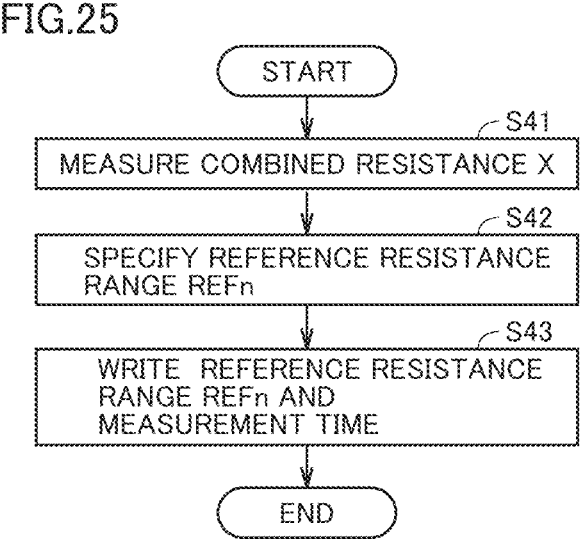
FIG. 25 is a flow chart of a process to record resistance value changes.

Next, a process to record resistance value changes is described with reference mainly to FIGS. 19, 24 and 25. FIG. 25 is a flow chart of a process to record resistance value changes. The process illustrated in FIG. 25 is periodically invoked at predefined regular intervals from a main routine not illustrated in the drawing and then carried out by analyzer 31. The steps (hereinafter, simply "S") are basically actualized through software processing by analyzer 31, however, may be actualized through hardware processing using, for example, an electronic circuit embedded in analyzer 31.

In S41, analyzer 31 measures the resistance value of sensor body 11A (may be hereinafter referred to as "combined resistance X"). The resistance value of sensor body 11A is a combined resistance value in which resistance values of three structures 122 (including metal thin films 8 and resistors 9), resistor 91, and wirings 41 and 42 are combined.

In S42, analyzer 31 specifies one of a plurality of reference resistance ranges REFn (n is an integer greater than or equal to 1) which is a range including combined resistance X measured in S41. The same number of reference resistance ranges REFn as the number of combination patterns of wire breakage/no wire breakage in the N number of structures (i.e., Nth power of 2) are set beforehand. In this example, eight (3rd power of 2) reference resistance ranges (reference resistance ranges REF1-REF8) are set beforehand.

For instance, reference resistance range REF1 is a range of combined resistance X when no wire breakage has occurred in any structure, which is set to a value substantially equal to the value of resistor 91 (100≤X<300). Reference resistance range REF2 is a range of combined resistance X when wire breakage has occurred in first structure 122A, which is set to 300≤X<500. Reference resistance range REF3 is a range of combined resistance X when wire breakage has occurred in second structure 122B, which is set to 500≤X<700. Reference resistance range REF4 is a range of combined resistance X when wire breakage has occurred in third structure 122C, which is set to 900≤X<1100.

Reference resistance range REF5 is a range of combined resistance X when wire breakage has occurred in first and second structures 122A and 122B, which is set to 700≤X<900. Reference resistance range REF6 is a range of combined resistance X when wire breakage has occurred in first and third structures 122A and 122C, which is set to 1100≤X<1300. Reference resistance range REF7 is a range of combined resistance X when wire breakage has occurred in second and third structures 122B and 122C, which is set to 1300≤X<1500.

Reference resistance range REF8 is a range of combined resistance X when wire breakage has occurred in first structure 122A, second structure 122B and third structure 122C, which is set to 1500≤ X.

In S43, analyzer 31 writes, as measured data, reference resistance range REFn specified in S42 and measurement time of combined resistance X in recorder 30.

When S43 is over, analyzer 31 ends the processing steps of FIG. 25.

Figure 26:
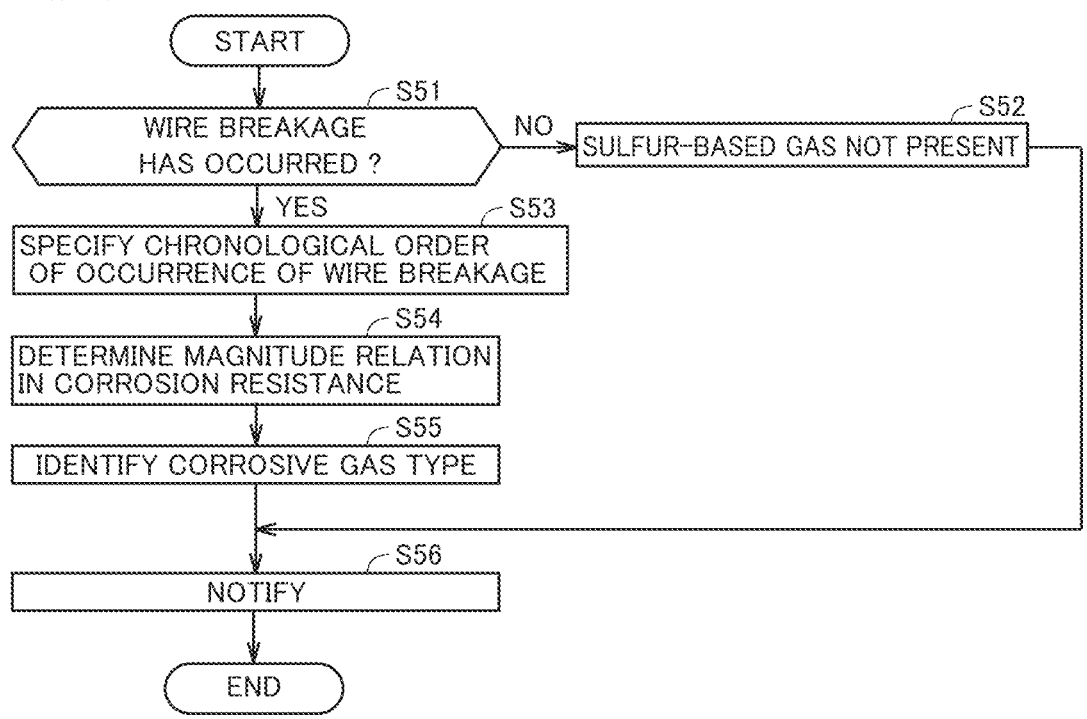
FIG. 26 is a flow chart of an exemplified analyzing process according to the fourth embodiment.

An analyzing process according to the fourth embodiment is hereinafter described with reference mainly to FIGS. 19, 24 and 26. FIG. 26 is a flow chart of an exemplified analyzing process according to the fourth embodiment. The process illustrated in FIG. 26 is periodically invoked at predefined regular intervals from a main routine not illustrated in the drawing and then carried out by analyzer 31. The periodic intervals at which the process of FIG. 26 is invoked may preferably be longer than the periodic intervals at which the process of FIG. 25 is invoked. The steps (hereinafter, simply "S") are basically actualized through software processing by analyzer 31, however, may be actualized through hardware processing using, for example, an electronic circuit embedded in analyzer 31.

In S51, analyzer 31 refers to the measured data stored in recorder 30 (reference resistance range REFn and measurement time of combined resistance X) to determine whether wire breakage has occurred. When the measured data is found to include at least one of reference resistance ranges REF2 to REF8, analyzer 31 determines that wire breakage has occurred. When wire breakage has occurred (YES in S51), analyzer 31 proceeds to S53. When no wire breakage has occurred (NO in S51), analyzer 31 proceeds to S52.

In S52, analyzer 31 determines that no sulfur-based gas is present.

In S53, analyzer 31 refers to the measured data stored in recorder 30 (reference resistance range REFn and measurement time of combined resistance X) to specify the chronological order of wire breakage that occurred by then. In recorder 30, all of reference resistance ranges REFn specified by then as well as measurement times of combined resistance X are stored. This may allow analyzer 31 to know specific changes of the reference resistance range. Analyzer 31 specifies the chronological order of wire breakage that occurred by then from the known changes of reference resistance range.

An example is given below, in which reference resistance ranges REF2 and REF5 are stored in recorder 30, and the measurement time of combined resistance X of reference resistance range REF2 precedes the measurement time of combined resistance X of reference resistance range REF5. This example may strongly suggest that wire breakage occurred in second structure 122B after the occurrence of wire breakage in first structure 122A. Then, analyzer 31 determines wire breakage occurred in second structure 122B after the occurrence of wire breakage in first structure 122A.

In S54, analyzer 31 may determine the magnitude relation in corrosion resistance between three structures 122 based on chronological order of wire breakage specified in S53. The corrosion resistance may be lower with an earlier occurrence of wire breakage. Analyzer 31, therefore, determines the magnitude relation in corrosion resistance between three structures 122 so that the corrosion resistance is lower with an earlier occurrence of wire breakage.

In S55, analyzer 31 identifies the type of any corrosive gas present in an environment similarly to the first embodiment (see S29 to S35).

In S56, analyzer 31 prompts notification device 40 to notify the obtained content. For example, analyzer 31 displays the content obtained in S52 or S55 on a liquid crystal display.

Following on from S52, analyzer 31 may display, on the liquid crystal display, such a message as "No sulfur-based gas", "No impact from sulfur-based gas" or "Ready for continued use". Following on from S52, analyzer 31 may not display any message on the liquid crystal display.

Following on from S55, analyzer 31 may display, on the liquid crystal display, such a message as "The corrosive gas is ***" or "Discuss any other cause of corrosion but sulfur-based gases".

When S56 is over, analyzer 31 ends the processing steps of FIG. 26.

Notification device 40 may be selected from such devices as LED indicator, buzzer and speaker.

Next, verification results on usefulness of sensor 101A according to the fourth embodiment are hereinafter described. In working examples described below, electric device 900A equipped with sensor 101A (inverter in these examples) was exposed in a corrosive gas-present environment. Sensor 101A includes three structures 122 described above (first structure 122A, second structure 122B, and third structure 122C). The material of metal thin film 8 in first structure 122A was copper. The material of metal thin film 8 in second and third structures 122B and 122C was silver. The metal thin films 8 of these three structures were all 10 μm in thickness. Coating material a1 of third structure 122C was a silicone-based resin having the oxygen permeability of 31000 [cc/m²·day at 20° C. (2 mm)] and having the thickness of 10 μm. The resistance value of resistor 9 in first structure 122A was 200Ω, the resistance value of resistor 9 in second structure 122B was 400Ω, the resistance value of resistor 9 in third structure 122C was 800Ω, and the resistance value of resistor 91 was 100Ω.

Fourth Embodiment, First Working Example

Electric device 900A was exposed in an environment under the condition of 40° C./95% RH/3 ppm $H_2S$. On day 1 after the exposure started, combined resistance X of sensor body 11A was 100Ω. At the time, none of the structures had experienced any wire breakage.

On day 6 after the exposure started, combined resistance X was 300Ω. On that day, the occurrence of wire breakage in first structure 122A was confirmed. The resistance value increase from 100Ω to 300Ω was thus proven to result from the wire breakage that occurred in first structure 122A.

On day 140 after the exposure started, combined resistance X of sensor body 11A was 700Ω. At the time, the occurrence of wire breakage in second structure 122B was confirmed, as well as in first structure 122A. The resistance value increase from 300Ω to 700Ω was thus proven to result from the wire breakage that additionally occurred in second structure 122B.

This verification result demonstrates that, in an environment where $H_2S$ is present and $S_8$ is not present (i.e., first environment), the magnitude relation in corrosion resistance between three structures may be defined as follows; first structure 122A<second structure 122B<third structure 122C.

Fourth Embodiment, Second Working Example

Electric device 900A was exposed in an environment at 75° C. where $S_8$ was present. On day 1 after the exposure started, combined resistance X of sensor body 11A was 100Ω. At the time, none of the structures had experienced any wire breakage.

On day 4 after the exposure started, combined resistance X of sensor body 11A was 900Ω. On that day, the occurrence of wire breakage in third structure 122C was confirmed. The resistance value increase from 100Ω to 900Ω was thus proven to result from the wire breakage that occurred in third structure 122C.

On day 7 after the exposure started, combined resistance X of sensor body 11A was 1300Ω. At the time, the occurrence of wire breakage in second structure 122B, as well as in third structure 122C, was confirmed. The resistance value increase from 900Ω to 1300Ω was thus proven to result from the wire breakage that additionally occurred in second structure 122B.

This verification result demonstrates that, in an environment where $S_8$ is present and $H_2S$ is not present (i.e., second environment), the magnitude relation in corrosion resistance between three structures is defined as follows; first structure 122A>second structure 122B>third structure 122C.

Fourth Embodiment, Third Working Example

Electric device 900A was exposed in an environment under the condition of 40° C./95% RH/(0.2 ppm $S_8$+3 ppm $H_2S$). On day 1 after the exposure started, combined resistance X of sensor body 11A was 100Ω. At the time, none of the structures had experienced any wire breakage.

On day 6 after the exposure started, combined resistance X of sensor body 11A was 300Ω. On that day, the occurrence of wire breakage in first structure 122A was confirmed. The resistance value increase from 100Ω to 300Ω was thus proven to result from the wire breakage that occurred in first structure 122A.

On day 8 after the exposure started, combined resistance X of sensor body 11A was 1100Ω. At the time, the occurrence of wire breakage in third structure 122C was confirmed, as well as in first structure 122A. The resistance value increase from 300Ω to 1100Ω was thus proven to result from the wire breakage that additionally occurred in third structure 122C.

This verification result demonstrates that, in an environment where $S_8$ and $H_2S$ coexist and the concentration of $H_2S$ is higher than that of $S_8$ (i.e., third environment), the magnitude relation in corrosion resistance between three structures is defined as follows; first structure 122A<third structure 122C<second structure 122B.

The verification results obtained from the first, second and third working examples of the fourth embodiment demonstrate that electric device 900A may be determined as being in the first environment, i.e., the type of corrosive gas present in the environment may be determined as a gas included in the other sulfur-based gases when the magnitude relation in corrosion resistance between three structures is defined as follows; first structure 122A<second structure 122B<third structure 122C.

These verification results also demonstrate that electric device 900A may be determined as being in the second environment, i.e., the type of corrosive gas present in the environment may be determined as sublimed sulfur when the magnitude relation in corrosion resistance between three structures is defined as follows; first structure 122A>second structure 122B>third structure 122C.

These verification results further demonstrate that electric device 900A may be determined as being in the third environment, i.e., sublimed sulfur and a gas included in the other sulfur-based gases coexist in the environment when the magnitude relation in corrosion resistance between three structures is defined as follows; first structure 122A<third structure 122C<second structure 122B.

According to the fourth embodiment, sensor 101A includes three structures 122, and the magnitude relation in corrosion resistance between three structures 122 differs between first environment, second environment, and third environment. According to the fourth embodiment, combined resistance X changes as a result of the occurrence of wire breakage, and the change of combined resistance X that occurred then is stored in recorder 30. Thus, the chronological order of wire breakage that occurred by then may be specified, which may allow the magnitude relation in corrosion resistance between three structures 122 to be successfully determined. Further, the type of corrosive gas present in the environment may be identifiable by comparing the determined magnitude relation in corrosion resistance between three structures 122 with the corrosion resistance information stored in recorder 30. Then, it can be determined whether one of the first type of corrosive gas and the second type of corrosive gas is present or the first type of corrosive gas and the second type of corrosive gas are coexistent.

According to the fourth embodiment, the resistance value of resistor 9 may be set to greater than that of metal thin film 8. Supposing that resistance measurer 20 has a poor measuring accuracy, failing to detect and measure any minor resistance value change of metal thin film 8, a structure with possible wire breakage may be identifiable based on changes of combined resistance X. Thus, it can be determined whether one of the first type of corrosive gas and the second type of corrosive gas is present or the first type of corrosive gas and the second type of corrosive gas are coexistent, regardless of whether resistance measurer 20 fails to provide a high accuracy in measurement.

Fifth Embodiment

In a fifth embodiment of this disclosure, analyzer 31 specifies wire breakage situation, more specifically, the presence or absence of wire breakage, from resistance values of the sensor body and identifies the type of corrosive gas present in the environment based on the specified presence or absence of wire breakage.

An electric device equipped with the sensor according to the fifth embodiment is configured similarly to electric device 900A according to the fourth embodiment (see FIG. 19). Analyzer 31 according to the fifth embodiment specifies wire breakage situation from the resistance value of sensor body 11A (combined resistance X) similarly to analyzer 31 according to the fourth embodiment. In the fifth embodiment, analyzer 31 does not write the measured combined resistance X in recorder 30, leaving no record of combined resistance X. The fifth embodiment fails to specify or grasp the chronological order of wire breakage. Analyzer 31 of the fifth embodiment, therefore, identifies the type of corrosive gas present in the environment by determining whether wire breakage has occurred or not at the present time.

The magnitude relation in corrosion resistance between three structures 122 is known to be similar to the magnitude relation in corrosion resistance between three structures 121 illustrated in FIG. 12 from the verification results of the first, second and third working examples of the fourth embodiment. In this embodiment, information on the magnitude relation in corrosion resistance between three structures 122 for each environment (i.e., corrosion resistance information) is stored in recorder 30 likewise.

Figure 27:
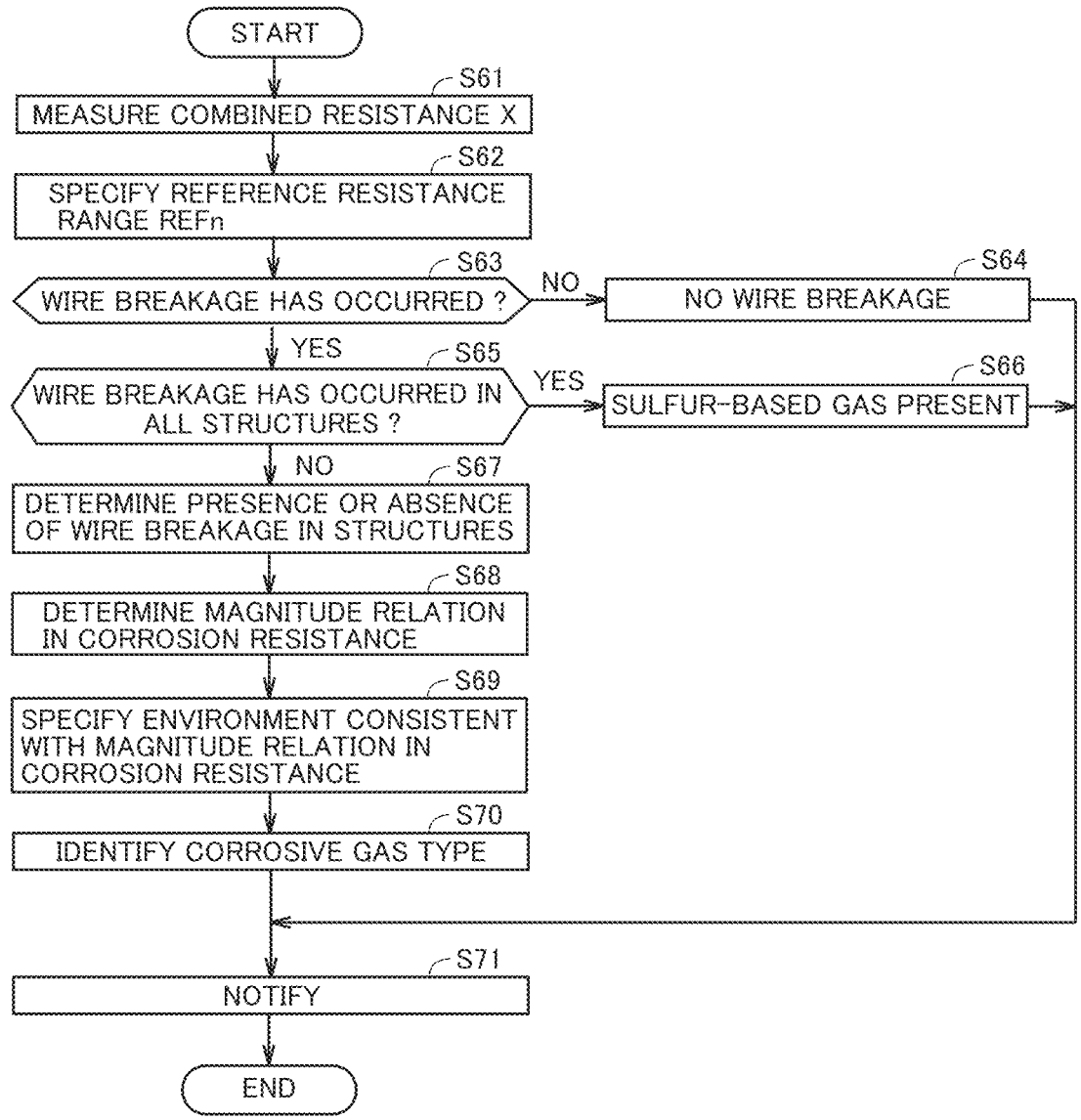
FIG. 27 is a flow chart of an exemplified analyzing process according to a fifth embodiment of this disclosure.

An analyzing process according to the fifth embodiment is hereinafter described with reference mainly to FIGS. 19, 24 and 27. FIG. 27 is a flow chart of an exemplified analyzing process according to the fifth embodiment. The process illustrated in FIG. 27 is periodically invoked at predefined regular intervals from a main routine not illustrated in the drawing and then carried out by analyzer 31. The steps (hereinafter, simply "S") are basically actualized through software processing by analyzer 31, however, may be actualized through hardware processing using, for example, an electronic circuit embedded in analyzer 31.

In S61, analyzer 31 measures combined resistance X at the time. In S62, analyzer 31 specifies reference resistance range REFn relevant to the measured combined resistance X. S61 and S62 are processing steps similar to S41 and S42.

In S63, analyzer 31 determines whether wire breakage has occurred or not. In case reference resistance range REFn specified in S62 is any range but reference resistance range REF1, analyzer 31 determines that wire breakage has occurred. When wire breakage has occurred (YES in S63), analyzer 31 proceeds to S65. When no wire breakage has occurred (NO in S63), analyzer 31 proceeds to S64.

In S64, analyzer 31 determines that no wire breakage has occurred.

In S65, analyzer 31 determines whether wire breakage has occurred in all of the structures. In case reference resistance range REFn specified in S62 is reference resistance range REF8, analyzer 31 determines that wire breakage has occurred in all of the structures. When wire breakage has occurred in all of the structures (YES in S65), analyzer 31 proceeds to S66. When wire breakage has not occurred in at least one of the structures (NO in S65), analyzer 31 proceeds to S67.

In S66, analyzer 31 determines that "at least one of sublimed sulfur and a gas included in the other sulfur-based gases", i.e., "a sulfur-based gas" is present.

In S67, analyzer 31 determines the presence or absence of wire breakage in the structures based on reference resistance range REFn specified in S62.

In S68, analyzer 31 determines the magnitude relation in corrosion resistance between three structures 122 based on the presence or absence of wire breakage determined in S67. Analyzer 31 determines the magnitude relation in corrosion resistance between three structures 122, so that any structure determined in S67 as wire breakage has occurred has a lower corrosion resistance than any other structure determined otherwise in S67.

Specifically, when wire breakage has occurred in only first structure 122A, analyzer 31 determines that first structure 122A has a lower corrosion resistance than second structure 122B and third structure 122C.

When wire breakage has occurred in only second structure 122B, analyzer 31 determines that second structure 122B has a lower corrosion resistance than first structure 122A and third structure 122C.

When wire breakage has occurred in only third structure 122C, analyzer 31 determines that third structure 122C has a lower corrosion resistance than first structure 122A and second structures 122B.

When wire breakage has occurred in only first structure 122A and second structure 122B, analyzer 31 determines that first structure 122A and second structure 122B have a lower corrosion resistance than third structure 122C.

When wire breakage has occurred in only first structure 122A and third structure 122C, analyzer 31 determines that first structure 122A and third structure 122C have a lower corrosion resistance than second structure 122B.

When wire breakage has occurred in only second structure 122B and third structure 122C, analyzer 31 determines that second structure 122B and third structure 122C have a lower corrosion resistance than first structure 122A.

In S69, analyzer 31 refers to the corrosion resistance information stored in recorder 30 to find and specify an environment consistent with the magnitude relation in corrosion resistance between three structures 122 determined in S68. When analyzer 31 fails to specify one environment consistent with the magnitude relation in corrosion resistance between three structures 122 determined in S68, analyzer 31 specifies all of the relevant environments.

In S70, analyzer 31 identifies the type of any corrosive gas present in the environment based on the environment specified in S69. For example, in case the environment specified in S69 is the first environment, analyzer 31 identifies the type of any corrosive gas present in this environment as a gas included in the other sulfur-based gases. In case the environment specified in S69 is the second environment, analyzer 31 identifies the type of any corrosive gas present in this environment as sublimed sulfur. In case the environment specified in S69 is the third environment, analyzer 31 identifies the type of any corrosive gas present in this environment as sublimed sulfur and a gas included in the other sulfur-based gases.

In case the environments specified in S69 are the first and third environments, analyzer 31 determines that a gas included in the other sulfur-based gases is at least present.

In S71, analyzer 31 prompts notification device 40 to notify the obtained content. For example, analyzer 31 displays the content obtained in S64, S66 or S70 on a liquid crystal display.

Following on from S64, analyzer 31 may display, on the liquid crystal display, such a message as "Wire breakage is currently undetectable".

Following on from S66, analyzer 31 may display, on the liquid crystal display, such a message as "A sulfur-based gas is present".

Following on from S70, analyzer 31 may display, on the liquid crystal display, such a message as "The corrosive gas is ***". When it is determined that a gas included in the other sulfur-based gases is at least present in S70, analyzer 31 displays, on the liquid crystal display, such a message as "a gas included in the other sulfur-based gases is present, with a possible presence of sublimed sulfur as well".

This embodiment, however, fails to specify the chronological order of wire breakage that occurred by then in case wire breakage has occurred in two structures. When, for example, wire breakage has occurred in both of first structure 122A and second structure 122B, wire breakage in second structure 122B may precede wire breakage in the other. When, for example, wire breakage has occurred in both of first structure 122A and third structure 122C, wire breakage in third structure 122C may precede wire breakage in the other. When, for example, wire breakage has occurred in both of second structure 122B and third structure 122C, wire breakage in second structure 122B may precede wire breakage in the other. When wire breakage has occurred in two structures, analyzer 31, in view of such possibly different timings of wire breakage, may display such messages as "The corrosive gas is ***", and "with a possible presence of corrosion factor other than sulfur-based gases".

When S71 is over, analyzer 31 ends the processing steps of FIG. 27.

Notification device 40 may be selected from such devices as LED indicator, buzzer and speaker.

Next, verification results on usefulness of sensor 101A according to the fifth embodiment are hereinafter described. This verification conducted employed the same conditions as those used to verify usefulness of the sensor of the fourth embodiment.

Fifth Embodiment, First Working Example

Electric device 900A was exposed in an environment under the condition of 40° C./95% RH/3 ppm $H_2S$. On day 1 after the exposure started, combined resistance X of sensor body 11A was 100Ω. At the time, none of the structures had experienced any wire breakage.

On day 6 after the exposure started, combined resistance X was 300Ω. On that day, the occurrence of wire breakage in first structure 122A was confirmed. The resistance value increase from 100Ω to 300Ω was thus proven to result from the wire breakage that occurred in first structure 122A.

Further, in an environment where $H_2S$ is present and $S_8$ is not present (i.e., first environment), first structure 122A was proven to have a lowest corrosion resistance among the three structures 122.

On day 140 after the exposure started, combined resistance X of sensor body 11A was 700Ω. At the time, the occurrence of wire breakage in second structure 122B was confirmed, as well as in first structure 122A. The resistance value increase from 100Ω to 700Ω was thus proven to result from the wire breakage that occurred in first structure 122A and second structure 122B.

Further, in an environment where $H_2S$ is present and $S_8$ is not present (i.e., first environment), first structure 122A and second structure 122B, among three structures 122, were proven to have a lower corrosion resistance than that of third structure 122C.

Fifth Embodiment, Second Working Example

Electric device 900A was exposed in an environment at 75° C. where $S_8$ was present. On day 1 after the exposure started, combined resistance X of sensor body 11A was 100Ω. At the time, none of the structures had experienced any wire breakage.

On day 4 after the exposure started, combined resistance X of sensor body 11A was 900Ω. On that day, the occurrence of wire breakage in third structure 122C was confirmed. The resistance value increase from 100Ω to 900Ω was thus proven to result from the wire breakage that occurred in third structure 122C.

Further, in an environment where $S_8$ is present and $H_2S$ is not present (i.e., second environment), third structure 122C was proven to have a lowest corrosion resistance among the three structures 122.

On day 7 after the exposure started, combined resistance X of sensor body 11A was 1300Ω. At the time, the occurrence of wire breakage in second structure 122B, as well as in third structure 122C, was confirmed. The resistance value increase from 100Ω to 1300Ω was thus proven to result from the wire breakage that occurred in second structure 122B and third structure 122C.

Further, in an environment where $S_8$ is present and $H_2S$ is not present (i.e., second environment), second structure 122B and third structure 122C, among three structures 122, were proven to have a lower corrosion resistance than that of first structure 122A.

Fifth Embodiment, Third Working Example

Electric device 900A was exposed in an environment under the condition of 40° C./95% RH/(0.2 ppm $S_8$+3 ppm H₂S). On day 1 after the exposure started, combined resistance X of sensor body 11A was 100Ω. At the time, none of the structures had experienced any wire breakage.

On day 6 after the exposure started, combined resistance X of sensor body 11A was 300Ω. On that day, the occurrence of wire breakage in first structure 122A was confirmed. The resistance value increase from 100Ω to 300Ω was thus proven to result from the wire breakage that occurred in first structure 122A.

Further, in an environment where $S_8$ and $H_2S$ coexist and the concentration of $H_2S$ is higher than that of $S_8$ (i.e., third environment), first structure 122A was proven to have a lowest corrosion resistance among the three structures 122.

On day 8 after the exposure started, combined resistance X of sensor body 11A was 1100Ω. At the time, the occurrence of wire breakage in third structure 122C was confirmed, as well as in first structure 122A. The resistance value increase from 100Ω to 1100Ω was thus proven to result from the wire breakage that occurred in first structure 122A and third structure 122C.

This verification result demonstrates that, in an environment where $S_8$ and $H_2S$ coexist and the concentration of $H_2S$ is higher than that of $S_8$ (i.e., third environment), first structure 122A and third structure 122C, among three structures 122, were proven to have a lower corrosion resistance than second structure 122B.

The verification results obtained from the first, second and third working examples of the fifth embodiment demonstrate that electric device 900A may be determined as being in the first environment or in the third environment, i.e., at least a gas included in the other sulfur-based gases is present in the environment when first structure 122A, among the three structures 122, has a lowest corrosion resistance.

These verification results also demonstrate that electric device 900A may be determined as being in the second environment, i.e., the type of corrosive gas present in the environment may be determined as sublimed sulfur when third structure 122C, among the three structures 122, has a lowest corrosion resistance.

These verification results further demonstrate that electric device 900A may be determined as being in the first environment, i.e., the type of corrosive gas present in the environment may be determined as a gas included in the other sulfur-based gases when first structure 122A and second structure 122B, among the three structures 122, have a lower corrosion resistance than third structure 122C.

These verification results further demonstrate that electric device 900A may be determined as being in the second environment, i.e., the type of corrosive gas present in the environment may be determined as sublimed sulfur when second structure 122B and third structure 122C, among the three structures 122, have a lower corrosion resistance than first structure 122A.

These verification results further demonstrate that electric device 900A may be determined as being in the third environment, i.e., the types of corrosive gases present in the environment may be determined as sublimed sulfur and a gas included in the other sulfur-based gases when first structure 122A and third structure 122C, among the three structures 122, have a lower corrosion resistance than second structure 122B.

According to the fifth embodiment, sensor 101A includes three structures 122, and the magnitude relation in corrosion resistance between three structures 122 differs between first environment, second environment, and third environment. According to the fifth embodiment, combined resistance X changes in response to the occurrence of wire breakage. Thus, whether wire breakage has occurred or not may be successfully determined, and the magnitude relation in corrosion resistance between three structures 122 may also be successfully determined. Further, the type of corrosive gas present in the environment may be identifiable by comparing the determined magnitude relation in corrosion resistance between three structures 122 with the corrosion resistance information stored in recorder 30. Then, it can be determined whether one of the first type of corrosive gas and the second type of corrosive gas is present or the first type of corrosive gas and the second type of corrosive gas are coexistent.

Sixth Embodiment

A sixth embodiment of this disclosure is targeted for more types of corrosive gases than in first to fifth embodiments. To be specific, target corrosive gases according to the sixth embodiment include sulfur-based gases and chlorine gas.

Figure 28:
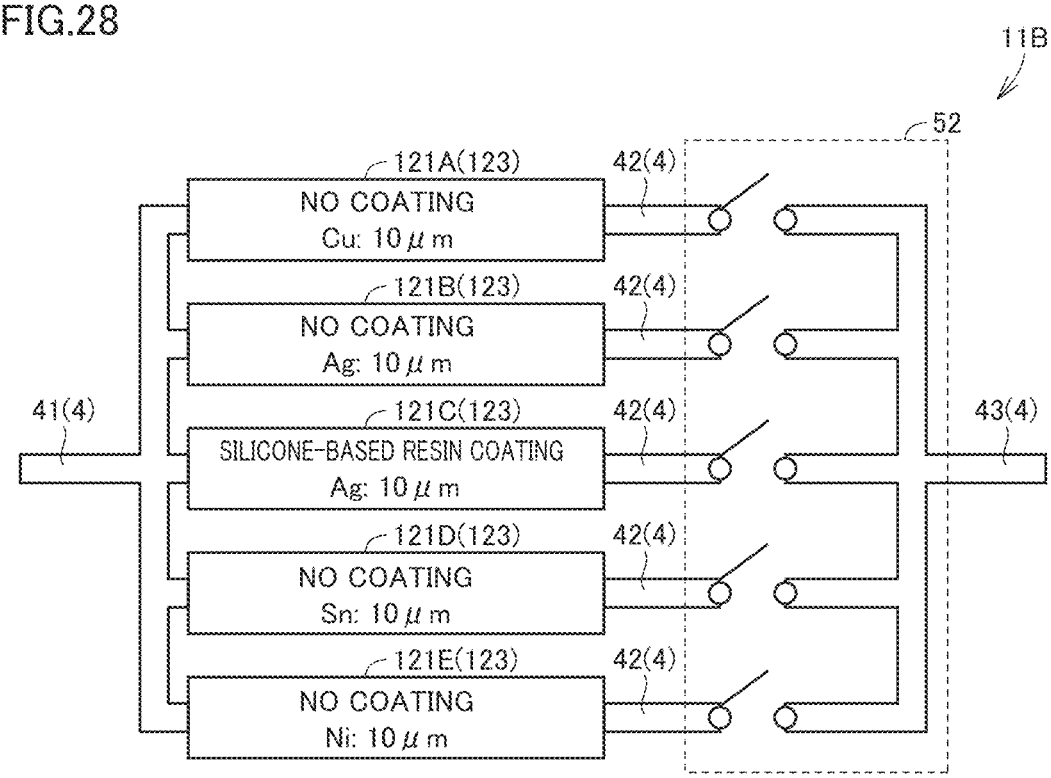
FIG. 28 is a drawing that illustrates an exemplified sensor body according to a sixth embodiment of this disclosure.

An electric device according to the sixth embodiment is configured similarly to electric device 900 according to the first embodiment (see FIG. 1) except that the sensor's body includes more structures than in the earlier embodiments. FIG. 28 is a drawing that illustrates an exemplified sensor body according to the sixth embodiment.

A sensor body 11B according to the sixth embodiment includes five structures (first structure 121A, second structure 121B, third structure 121C, fourth structure 121D, and fifth structure 121E), wirings 4, and terminal changer 52. In the description given below, first structure 121A, second structure 121B, third structure 121C, fourth structure 121D and fifth structure 121E may be collectively referred to as five structures 123.

Wirings 4 include a wiring 41, five wirings 42 and a wiring 43. Wirings 4 are routed on a circuit board. Five wirings 42 are routed correspondingly to five structures 123. The structures are each disposed so that wiring 41 is connectable to a corresponding one of wirings 42 and are mounted onto wirings 41 and 42 by soldering.

First structure 121A, second structure 121B and third structure 121C are configured as described thus far. Fourth structure 121D and fifth structure 121E are similar to first structure 121A except that metal thin films in these structures are made of different metallic materials.

To be specific, fourth structure 121D includes a metal thin film, specifically, a thin film made of tin, and this thin film is exposed in an environment. Tin is an example of the "third metallic material" as described herein. Chlorine gas preferentially corrodes tin.

Fifth structure 121E includes a metal thin film, specifically, a thin film made of nickel, and this thin film is exposed in the environment. Nickel is corrodible by sulfur dioxide and also by chlorine gas.

The metal thin films of these five structures 123 are all 10 μm in thickness. The coating material is also 10 μm in thickness. Instead, the metal thin films of these five structures 123 may have different thicknesses. The metal thin films and the coating material may have different thicknesses.

As described above, the magnitude relation in corrosion resistance between first structure 121A, second structure 121B and third structure 121C differs between the first environment, the second environment, and the third environment.

In this embodiment, as information on the magnitude relation in corrosion resistance between first structure 121A, second structure 121B and third structure 121C for each environment (i.e., corrosion resistance information), the magnitude relation illustrated in FIG. 12 is stored in recorder 30. In this embodiment, analyzer 31 calculates the corrosion speed of each of five structures 123 in an environment where sensor 101 (or electric device 900) is really exposed.

In view of the fact that chlorine gas preferentially corrodes tin, analyzer 31 determines whether chlorine gas is present based on the corrosion speed of fourth structure 121D. In view of the fact that nickel is corrodible by sulfur dioxide and also by chlorine gas, analyzer 31 determines whether sulfur dioxide is present based on the corrosion speeds of fourth structure 121D and fifth structure 121E.

Analyzer 31 determines the magnitude relation in corrosion resistance between first structure 121A, second structure 121B and third structure 121C based on the corrosion speeds of these structures and then determines whether one of sublimed sulfur and hydrogen sulfide is present or sublimed sulfur and hydrogen sulfide are coexistent as described in the first embodiment.

The materials and thicknesses of the metal thin film and of the coating material described so far are just a few examples. The materials and thicknesses of the metal thin film and of the coating material may be set otherwise insofar as the magnitude relation in corrosion resistance between first structure 121A, second structure 121B and third structure 121C differs between the first environment, the second environment and the third environment.

An analyzing process according to the sixth embodiment is described below with reference to FIGS. 1 and 28 to 29. FIG. 29 is a flow chart of an exemplified analyzing process according to the sixth embodiment. The process illustrated in FIG. 29 is periodically invoked at predefined regular intervals from a main routine not illustrated in the drawing and then carried out by analyzer 31. The steps (hereinafter, simply "S") are basically actualized through software processing by analyzer 31, however, may be actualized through hardware processing using, for example, an electronic circuit embedded in analyzer 31.

In S81, analyzer 31 calculates the corrosion speeds of five structures 123 using the method described in the first embodiment or second embodiment and then writes the calculated corrosion speeds in recorder 30.

In S82, analyzer 31 extracts, from recorder 30, the latest corrosion speeds of these five structures 123.

In S83, analyzer 31 determines whether corrosion speed $V_{121D}$ of fourth structure 121D is zero. S83 is a step of determining whether chlorine gas is present. It can be determined that chlorine gas is not present when corrosion speed of fourth structure 121D including a tin-made thin film preferentially corroded by chlorine gas is zero. When corrosion speed $V_{121D}$ is zero (YES in S83), analyzer 31 proceeds to S85. When corrosion speed $V_{121D}$ is not zero (NO in S83), analyzer 31 proceeds to S84.

In S84, analyzer 31 determines that chlorine gas is present. Chlorine gas corrodes most of the metallic materials, which makes it difficult to accurately evaluate impacts of any other corrosive gases but chlorine gas. When the presence of chlorine gas is confirmed, therefore, analyzer 31 does not determine whether any other corrosive gases but chlorine gas is present.

In S85, analyzer 31 determines whether corrosion speed $V_{121E}$ of fifth structure 121E is zero. S85 is a step of determining whether sulfur dioxide is present. Nickel is corrodible by sulfur dioxide and also by chlorine gas. S85 is performed in a case of YES in S83, i.e., in the absence of chlorine gas. Thus, whether sulfur dioxide is present may be determined based on corrosion speed $V_{121E}$. When corrosion speed $V_{121E}$ is zero, it can be determined that sulfur dioxide is not present. When corrosion speed $V_{121E}$ is zero (YES in S85), analyzer 31 proceeds to S87. When corrosion speed $V_{121E}$ is not zero (NO in S85), analyzer 31 proceeds to S86.

In S86, analyzer 31 determines that sulfur dioxide is present. Copper is corrodible by sulfur dioxide, whereas silver is hardly affected by sulfur dioxide. When the presence of sulfur dioxide is confirmed, therefore, analyzer 31 further determines whether sublimed sulfur is coexistent with sulfur dioxide based on the corrosion speeds of second structure 121B and third structure 121C (S88-S92).

In S87, analyzer 31 carries out S28 to S35 described in the first embodiment (see FIG. 15) to determine the presence or absence of hydrogen sulfide and sublimed sulfur. In the sixth embodiment, in S30, analyzer 31 identifies the type of corrosive gas present in the environment as hydrogen sulfide. In the sixth embodiment, in S34, analyzer 31 identifies the types of corrosive gases present in the environment as sublimed sulfur and hydrogen sulfide.

In S88, analyzer 31 determines whether corrosion speeds $V_{121B}$ and $V_{121C}$ are both zero. When corrosion speeds $V_{121B}$ and $V_{121C}$ are both zero (YES in S88), analyzer 31 proceeds to S89. When at least one of corrosion speeds $V_{121B}$ and $V_{121C}$ is not zero (NO in S88), analyzer 31 proceeds to S90.

In S89, analyzer 31 identifies the type of corrosive gas present in the environment as sulfur dioxide, determining that neither of hydrogen sulfide nor sublimed sulfur is present in the environment.

In S90, analyzer 31 determines whether corrosion speed $V_{121B}$>corrosion speed $V_{121C}$ is satisfied. The relation of corrosion speed $V_{121B}$>corrosion speed $V_{121C}$ may be satisfied when the magnitude relation in corrosion resistance between second structure 121B and third structure 121C is defined as follows; second structure 121B<third structure 121C, i.e., sensor 101 (or electric device 900) is exposed in the first environment. When corrosion speed $V_{121B}$>corrosion speed $V_{121C}$ is satisfied (YES in S90), analyzer 31 proceeds to S91. When corrosion speed $V_{121B}$>corrosion speed $V_{121C}$ is not satisfied (NO in S90), analyzer 31 proceeds to S92.

In S91, analyzer 31 determines that hydrogen sulfide may possibly be present, along with sulfur dioxide, in the environment. Specifically, analyzer 31 determines that, in the environment, sulfur dioxide is present and sublimed sulfur is not present, and hydrogen sulfide may be present in addition to sulfur dioxide.

In S92, analyzer 31 determines that sublimed sulfur is present, along with sulfur dioxide, in the environment.

In S93, analyzer 31 prompts notification device 40 to notify the obtained content. For example, analyzer 31 displays the content obtained in S84, S87, S89, S91 or S92 on a liquid crystal display.

Following on from S84, analyzer 31 may display, on the liquid crystal display, such a message as "Chlorine gas is present".

Following on from S87, analyzer 31 may display, on the liquid crystal display, such a message as "The corrosive gas is ***" or "Discuss any other cause of corrosion but sulfur-based gases".

Following on from S89, analyzer 31 may display, on the liquid crystal display, such a message as "Sulfur dioxide is present, and sublimed sulfur and hydrogen sulfide is not present".

Following on from S91, analyzer 31 may display, on the liquid crystal display, such a message as "Hydrogen sulfide may possibly be present, along with sulfur dioxide, in the environment".

Following on from S92, analyzer 31 may display, on the liquid crystal display, such a message as "Sublimed sulfur is present, along with sulfur dioxide, in the environment".

When S93 is over, analyzer 31 ends a sequence of steps illustrated in FIG. 29.

Notification device 40 may be selected from such devices as LED indicator, buzzer and speaker.

The sixth embodiment may be thus allowed to not only determine whether one of the first type of corrosive gas and the second type of corrosive gas is present or the first type of corrosive gas and the second type of corrosive gas are coexistent but also determine whether a third type of corrosive gas exists.

Thus far were described various embodiments of the technology disclosed herein. As in the description given so far, it can be determined whether one of the first type of corrosive gas and the second type of corrosive gas is present or the first type of corrosive gas and the second type of corrosive gas are coexistent. The embodiments disclosed herein described how to determine whether one of sublimed sulfur and a gas included in the other sulfur-based gases is present or sublimed sulfur and a gas included in the other sulfur-based gases are coexistent.

The other sulfur-based gases and sublimed sulfur corrode similar types of metals. This may be a problem with the technologies described in patent literatures 1 and 2 (PTL 1 and 2), failing to determine whether one of sublimed sulfur and a gas included in the other sulfur-based gases is present or sublimed sulfur and a gas included in the other sulfur-based gases are coexistent. Gas-induced corrosion factors may typically include metal-corrosive gas combination (metal corrosiveness), and corrosive gas concentration, temperature, and humidity. This may be directly applied to corrosiveness induced by hydrogen sulfide or sulfur dioxide, in which case corrosion speed increases with a greater value of each corrosion factor. On the other hand, corrosion induced by sublimed sulfur may be hardly affected by humidity. One way to improve environmental corrosiveness may be humidity reduction using air conditioning. This may be useful for hydrogen sulfide and sulfur dioxide but may hardly have any effect on sublimed sulfur. Thus, whether sublimed sulfur and the other sulfur-based gases are coexistent with each other may be useful information for improvement of environmental corrosiveness. As disclosed herein, it can be determined whether one of sublimed sulfur and a gas included in the other sulfur-based gases is present or sublimed sulfur and a gas included in the other sulfur-based gases are coexistent, which may offer information useful for improvements of environmental corrosiveness.

All of the embodiments are disclosed herein by way of illustration and example only and should not be construed as limiting by any means the scope of this disclosure. The scope of this disclosure is solely defined by the appended claims and is intended to cover the claims, equivalents, and all of possible modifications made without departing the scope of this disclosure.

REFERENCE SIGNS LIST

3: circuit board, 4, 41, 42, 43: wiring, 5: solder, 6: insulating substrate, 7: electrode pair, 8: metal thin film, 9, 91: resistor, 11, 11A, 11B: sensor body, 12: temperature-humidity sensor, 20: resistance measurer, 30: recorder, 31: analyzer, 40: notification device, 52: terminal changer, 71: first electrode, 72: second electrode, 90: electric device body, 101, 101A: sensor, 121A, 122A: first structure, 121B, 122B: second structure, 121C, 122C: third structure, 121D: fourth structure, 121E: fifth structure, 201: voltmeter, 202: ammeter, 900, 900A: electric device, a1: coating material

The invention claimed is:

1. A sensor to identify a type of a corrosive gas present in an environment, the type of the corrosive gas at least including a first type and a second type, the sensor comprising:
   a sensor body comprising at least three structures;
   a measurer to measure a resistance value of each of the at least three structures or a resistance value of the sensor body;
   an analyzer to identify the type of the corrosive gas present in the environment based on the resistance value measured by the measurer and corrosion resistance information that represents a magnitude relation in corrosion resistance between the at least three structures for each environment; and
   a notification device to notify a content identified by the analyzer,
   the at least three structures comprising:
   a first structure comprising a thin film including a first metallic material, the thin film being exposed in the environment;
   a second structure comprising a thin film including a second metallic material that differs from the first metallic material, the thin film being exposed in the environment; and
   a third structure comprising a thin film including the second metallic material, a surface of the thin film exposed in the environment being covered with a coating material,
   the corrosive gas of the first type and the corrosive gas of the second type each causing corrosion of the first metallic material and the second metallic material, wherein
   the magnitude relation in corrosion resistance between the at least three structures differs between a first environment, a second environment, and a third environment,
   the corrosive gas of the first type is present and the corrosive gas of the second type is not present in the first environment,
   the corrosive gas of the second type is present and the corrosive gas of the first type is not present in the second environment, and
   the corrosive gas of the first type and the corrosive gas of the second type are both present in the third environment, wherein
   the coating material decreases the corrosion speed of the thin film including the second metallic material and covered with the coating material, in the first environment,
   the coating material increases the corrosion speed of the thin film including the second metallic material and covered with the coating material, in the second environment and the third environment, and
   the first metallic material has a lower corrosion resistance to the corrosive gas of the first type than the second metallic material.

2. The sensor according to claim 1, wherein the measurer measures the resistance value of each of the at least three structures,
   the analyzer calculates a corrosion speed or a corrosion ratio of each of the at least three structures based on the resistance value measured by the measurer, the analyzer determines the magnitude relation in corrosion resistance between the at least three structures based on the calculated corrosion speed or the calculated corrosion ratio, and the analyzer identifies the type of the corrosive gas present in the environment based on the corrosion resistance information and the determined magnitude relation in corrosion resistance between the at least three structures.

3. The sensor according to claim 2, further comprising a storage in which the resistance value measured by the measurer and measurement time when the resistance value was measured by the measurer are stored in association with each other, wherein the measurer measures the resistance value of each of the at least three structures periodically at predefined intervals, and the analyzer calculates the corrosion speed or the corrosion ratio of each of the at least three structures based on a resistance value measured at a first measurement time and a resistance value measured at a second measurement time that is an arbitrary time before the first measurement time.

4. The sensor according to claim 3, wherein
the analyzer further calculates a concentration of the corrosive gas present in the environment based on a temperature in the environment, a humidity in the environment, and the calculated corrosion speed, and
the notification device further notifies the concentration of the corrosive gas calculated by the analyzer.

5. The sensor according to claim 4, wherein
the analyzer calculates the concentration of the corrosive gas present in the environment by substituting the temperature in the environment, the humidity in the environment, and the calculated corrosion speed in a formula, and
the formula is formulated using analysis of variance based on corrosion speeds of the thin film obtained in a plurality of model environments that differ in at least one of a temperature, a humidity, and a concentration of the corrosive gas.

6. The sensor according to claim 5, wherein
the type of the corrosive gas further includes a third type,
the at least three structures further comprise a fourth structure comprising a thin film including a third metallic material that differs from the first metallic material and the second metallic material, the thin film being exposed in the environment,
the corrosive gas of the third type preferentially causes corrosion of the third metallic material.

7. The sensor according to claim 4, wherein
the type of the corrosive gas further includes a third type,
the at least three structures further comprise a fourth structure comprising a thin film including a third metallic material that differs from the first metallic material and the second metallic material, the thin film being exposed in the environment,
the corrosive gas of the third type preferentially causes corrosion of the third metallic material.

8. The sensor according to claim 3, wherein
the type of the corrosive gas further includes a third type,
the at least three structures further comprise a fourth structure comprising a thin film including a third metallic material that differs from the first metallic material and the second metallic material, the thin film being exposed in the environment,
the corrosive gas of the third type preferentially causes corrosion of the third metallic material.

9. The sensor according to claim 2, wherein
the analyzer further calculates a concentration of the corrosive gas present in the environment based on a temperature in the environment, a humidity in the environment, and the calculated corrosion speed, and
the notification device further notifies the concentration of the corrosive gas calculated by the analyzer.

10. The sensor according to claim 9, wherein
the analyzer calculates the concentration of the corrosive gas present in the environment by substituting the temperature in the environment, the humidity in the environment, and the calculated corrosion speed in a formula, and
the formula is formulated using analysis of variance based on corrosion speeds of the thin film obtained in a plurality of model environments that differ in at least one of a temperature, a humidity, and a concentration of the corrosive gas.

11. The sensor according to claim 10, wherein
the type of the corrosive gas further includes a third type,
the at least three structures further comprise a fourth structure comprising a thin film including a third metallic material that differs from the first metallic material and the second metallic material, the thin film being exposed in the environment,
the corrosive gas of the third type preferentially causes corrosion of the third metallic material.

12. The sensor according to claim 9, wherein
the type of the corrosive gas further includes a third type,
the at least three structures further comprise a fourth structure comprising a thin film including a third metallic material that differs from the first metallic material and the second metallic material, the thin film being exposed in the environment,
the corrosive gas of the third type preferentially causes corrosion of the third metallic material.

13. The sensor according to claim 2, wherein
the type of the corrosive gas further includes a third type,
the at least three structures further comprise a fourth structure comprising a thin film including a third metallic material that differs from the first metallic material and the second metallic material, the thin film being exposed in the environment,
the corrosive gas of the third type preferentially causes corrosion of the third metallic material.

14. The sensor according to claim 1, wherein
each of the at least three structures further comprises a resistor connected in parallel to the thin film,
the resistor of an optional one of the at least three structures has a resistance value that differs from a resistance value of a resistor in each of the rest of the at least three structures and that differs from a total of respective resistance values of resistors in optionally selected ones of the rest of the at least three structures,
the measurer measures a resistance value of the sensor body,
the analyzer specifies wire breakage situation in the at least three structures based on the resistance value measured by the measurer,
the analyzer determines the magnitude relation in corrosion resistance between the at least three structures based on the specified wire breakage situation, and
the analyzer identifies the type of the corrosive gas present in the environment based on the corrosion resistance information and the determined magnitude relation in corrosion resistance between the at least three structures.

15. The sensor according to claim 14, wherein the wire breakage situation is a chronological order of occurrence of wire breakage in the at least three structures.

16. The sensor according to claim 14, wherein the wire breakage situation is presence or absence of wire breakage in the at least three structures.

17. The sensor according to claim 1, wherein
the type of the corrosive gas further includes a third type,
the at least three structures further comprise a fourth structure comprising a thin film including a third metallic material that differs from the first metallic material and the second metallic material, the thin film being exposed in the environment,
the corrosive gas of the third type preferentially causes corrosion of the third metallic material.

18. The sensor according to claim 1, wherein the coating material includes a silicone-based resin.

19. The sensor according to claim 1, wherein the thin films in the at least three structures are equal in thickness.

20. An electric device comprising the sensor according to claim 1.

* * * * *